US008366894B2

(12) United States Patent  (10) Patent No.: US 8,366,894 B2
Manoukian et al.  (45) Date of Patent: Feb. 5, 2013

(54) MULTI-GAS MICROSENSOR ASSEMBLY

(75) Inventors: Mourad Manoukian, Watertown, MA (US); Anthony B. LaConti, Lynnfield, MA (US); W. Michael Krebs, Sudbury, MA (US); Linda A. Tempelman, Lincoln, MA (US); John W. Forchione, Jr., Ashland, MA (US); Erich Muehlanger, Jr., East Boston, MA (US)

(73) Assignee: Giner, Inc., Newton, MA (US)

( * ) Notice: Subject to any disclaimer, the term of this patent is extended or adjusted under 35 U.S.C. 154(b) by 357 days.

(21) Appl. No.: 12/660,197

(22) Filed: Feb. 22, 2010

(65) Prior Publication Data

US 2010/0276287 A1   Nov. 4, 2010

Related U.S. Application Data

(60) Provisional application No. 61/208,129, filed on Feb. 20, 2009.

(51) Int. Cl.
*G01N 27/26* (2006.01)
*G01N 27/407* (2006.01)

(52) U.S. Cl. ........ 204/426; 204/412; 204/424; 204/431; 204/432

(58) Field of Classification Search ............... 204/412, 204/421–429, 431, 432
See application file for complete search history.

(56) References Cited

U.S. PATENT DOCUMENTS

| | | | |
|---|---|---|---|
| 4,913,792 A * | 4/1990 | Nagata et al. .................. 204/412 |
| 5,298,146 A * | 3/1994 | Braden et al. ................. 204/406 |
| 5,518,602 A | 5/1996 | Kessel | |
| 5,527,446 A | 6/1996 | Kosek et al. | |
| 5,746,900 A * | 5/1998 | Venkatasetty ................. 204/415 |
| 6,007,697 A | 12/1999 | Yagi et al. | |
| 2002/0019448 A1 | 2/2002 | Sugaya et al. | |
| 2002/0098332 A1* | 7/2002 | Warren et al. ................. 428/209 |
| 2003/0085125 A1 | 5/2003 | Prohaska et al. | |
| 2004/0129565 A1* | 7/2004 | Prohaska et al. ............. 204/424 |
| 2005/0029124 A1 | 2/2005 | Holmes et al. | |
| 2005/0230767 A1* | 10/2005 | Park et al. ..................... 257/414 |
| 2006/0096871 A1* | 5/2006 | Manoukian et al. .......... 205/782 |
| 2007/0131864 A1* | 6/2007 | Ellis et al. ..................... 250/343 |
| 2008/0127726 A1* | 6/2008 | Elkins ........................ 73/152.42 |

* cited by examiner

*Primary Examiner* — J. Christopher Ball
*Assistant Examiner* — Jennifer Dieterle
(74) *Attorney, Agent, or Firm* — Kriegsman & Kriegsman

(57) ABSTRACT

A multi-gas microsensor assembly for simultaneously detecting carbon dioxide and oxygen in real time. According to one embodiment, the assembly comprises a non-conductive, solid substrate. A plurality of sensing electrodes, a single reference electrode, and a single counter electrode are positioned on one side of the non-conductive, solid substrate. In addition, all of the electrodes are in intimate contact with the same side of a solid-polymer electrolyte anion-exchange membrane, the solid polymer electrolyte membrane having at least one gas diffusion opening aligned with each sensing electrode. The sensor is operated in a three-electrode potentiostatic mode, in which a constant potential is maintained between the sensing and reference electrodes, and the current is measured between the sensing and counter electrodes. Control of the electrodes is achieved with a small bi-potentiostat. The design of the bi-potentiostat allows at least two different sensing electrodes to share the same counter and reference electrodes.

31 Claims, 18 Drawing Sheets

Response curve of the microsensor for simultaneous detection of $CO_2$ and $O_2$ concentrations

MULTI-GAS MICROSENSOR ASSEMBLY

CROSS-REFERENCE TO RELATED APPLICATIONS

The present application claims the benefit under 35 U.S.C. 119(e) of U.S. Provisional Patent Application No. 61/208,129, filed Feb. 20, 2009, the disclosure of which is incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract Nos. NBCHC060123 and NBCHC070121 awarded by the Department of Homeland Security.

BACKGROUND OF THE INVENTION

The present invention relates generally to electrochemical gas sensors and relates more particularly to an electrochemical multi-gas microsensor which may be used to detect, for example, carbon dioxide and oxygen. The present invention may be used in the environmental, medical, agricultural, bio-related and food industries, including the food packaging and the brewing and carbonated drinks industries.

Carbon dioxide ($CO_2$) is a colorless, odorless and non-combustible gas and is one of the most important gases on the planet. Plants use $CO_2$, people exhale $CO_2$, and $CO_2$ is one of the most plentiful by-products of the combustion process in devices ranging from furnaces to lawn mowers to coal-fired electrical power plants. When present in high concentrations in the air (greater than 70,000 parts per million (ppm)) it acts primarily as a simple asphyxiant without other physiological effects. In indoor environments, it is primarily produced by human metabolism and is exhaled through the lungs.

Monitoring of carbon dioxide emissions from various natural and industrial sources to the environment facilitates a better understanding of the fate of the carbon dioxide in the global carbon cycle. In indoor environments, monitoring carbon dioxide levels provides for a better quality indoor air through feedback control demand ventilation systems.

Also, monitoring of carbon dioxide levels in patients in a hospital or clinical setting is important because of the central role of carbon dioxide in physiology. Carbon dioxide is a product of the oxidation of energy sources at the cellular level; carbon dioxide is transported in blood and, for the most part, eliminated through the lungs. Thus, it is involved in tissue perfusion and metabolism, systemic circulation, lung perfusion and ventilation. It is reasonable to expect that any changes in those basic functions might be indicated or marked by changes in expired $CO_2$, usually expressed as the end tidal partial pressure of $CO_2$ (pet$CO_2$), measured as the plateau section in a capnograph. In addition to end tidal monitoring of carbon dioxide levels in patients, transdermal and sublingual monitoring are alternative methods that provide good correlation with blood carbon dioxide levels.

Furthermore, monitoring of carbon dioxide levels is important in agricultural and bio-related process applications, in the food packaging industry, and in the brewing and carbonated drinks industry. In particular, in agricultural and bio-related process applications, the growth rate and development of plants can be improved by controlling the concentration of carbon dioxide. In greenhouses and mushroom farms, the growth rate and development of mushrooms and plants can be improved by controlling the concentration of carbon dioxide. This raises the productivity and quality of the crops. Furthermore, measuring and monitoring of dissolved carbon dioxide levels in plant cell culture bioreactors is important for plant physiology research. In the food packaging industry, adding carbon dioxide to food packaging can considerably extend the storage and shelf life of meat, cheese, as well as fruits and vegetables. In the meat packaging industry, a high concentration of $CO_2$ in the packaging inhibits bacterial growth and retains the natural color of the meat. In the brewing and carbonated drinks industry, the measurement and control of carbon dioxide level is important in these beverage applications.

In addition to the applications listed above, measurement and control of carbon dioxide levels are important wherever dry ice is produced, handled and used (e.g., food freezing, cold storage, cargo ships, and dry-ice production facilities).

In U.S. Patent Application Publication No. US 2006/0096871 A1, inventors Manoukian et al., which was published May 11, 2006, and which is incorporated herein by reference, there is disclosed an electrochemical sensor designed to detect carbon dioxide gas. The sensor includes a non-conductive solid substrate. A sensing electrode, a reference electrode, and a counter electrode are positioned on the substrate. A solid polymer electrolyte anion-exchange membrane is in intimate contact with the sensing electrode, the reference electrode, and the counter electrode.

Carbon dioxide is not the only gas that is routinely monitored. Oxygen is routinely monitored in gas mixtures in patients who are under anesthesia or whose breathing is being controlled by mechanical ventilators to ensure that the prescribed level of oxygen is being delivered. In addition to the more safety-related function of oxygen monitoring, there is considerable interest in monitoring oxygen in expired breath to provide diagnostic information on lung function during and after surgery.

There is a growing recognition in academic and industrial biotechnology that finer manipulation of the dissolved oxygen and carbon dioxide levels in mammalian cell bioreactors may be advantageous. In addition, in the fields of tissue engineering and bio-hybrid devices, it may be necessary to culture cells at or near physiological conditions in order to grow cells that will thrive once transplanted into the human body. Accurate, on-line, convenient measurement of dissolved $O_2$ and $CO_2$ would be a first step in optimizing mammalian cell bioreactors.

There is a large number of carbon dioxide and oxygen detectors on the market today designed for environmental, medical, biomedical, food and safety monitoring applications. However, it is believed that there is no sensor module that combines detection of carbon dioxide and oxygen simultaneously and in real time in one sensor cell and module.

Patents and publications of interest include the following, all of which are incorporated herein by reference: U.S. Patent Application Publication No. US 2004/0129565 A1, inventors Prohaska et al., published Jul. 8, 2004; U.S. Pat. No. 5,518,602, inventor Kessel, issued May 21, 1996; U.S. Pat. No. 5,527,446, inventors Kosek et al., issued Jun. 18, 1996; U.S. Pat. No. 6,007,697, inventors Yagi et al., issued Dec. 28, 1999; U.S. Patent Application Publication No. US 2005/0029124 A1, inventors Holmes et al., published Feb. 10, 2005; U.S. Patent Application Publication No. US 2002/0019448 A1, inventors Sugaya et al., published Feb. 14, 2002; and U.S.

Patent Application No. US 2003/0085125 A1, inventors Prohaska et al., published May 8, 2003.

SUMMARY OF THE INVENTION

It is an object of the present invention to provide a novel gas sensor.

It is another of the present invention to provide a gas sensor as described above that is an electrochemical gas sensor.

It is still another object of the present invention to provide a gas sensor as described above that is capable of simultaneously detecting two or more gases in real time in one sensor module.

Therefore, according to one aspect of the invention, there is provided a multi-gas sensor, the multi-gas sensor comprising (a) a non-conductive solid substrate, said non-conductive solid substrate having a first side; (b) a plurality of sensing electrodes, each of said sensing electrodes being positioned on said first side of said non-conductive solid substrate; (c) a reference electrode, said reference electrode being positioned on said first side of said non-conductive solid substrate; (d) a counter electrode, said counter electrode being positioned on said first side of said non-conductive solid substrate; (e) wherein at least two of said sensing electrodes share said reference electrode and said counter electrode; and (f) a solid polymer electrolyte ion-exchange membrane, said solid polymer electrolyte ion-exchange membrane being in intimate contact with said sensing electrodes, said reference electrode, and said counter electrode, said solid polymer electrolyte ion-exchange membrane having at least one gas diffusion opening aligned with each of said sensing electrodes.

The present invention is also directed at a multi-gas microsensor assembly, said multi-gas microsensor assembly comprising (a) a multi-gas sensor of the type described above; and (b) a multi-potentiostat, the multi-potentiostat simultaneously and independently controlling two or more of the sensing electrodes of the multi-gas sensor.

The present invention is additionally directed at a multi-gas microsensor assembly, said multi-gas microsensor assembly comprising (a) a sensor module, said sensor module comprising (i) a sensor, said sensor comprising (A) a non-conductive solid substrate, (B) a plurality of sensing electrodes positioned on said non-conductive solid substrate, (C) a reference electrode positioned on said non-conductive solid substrate, (D) a counter electrode positioned on said non-conductive solid substrate, (E) wherein at least two of said sensing electrodes share said reference electrode and said counter electrode, (F) a solid polymer electrolyte ion-exchange membrane in intimate contact with said sensing electrodes, said reference electrode, and said counter electrode, said solid polymer electrolyte ion-exchange membrane having at least one gas diffusion opening aligned with each of said sensing electrodes, and (ii) a sensor housing, the sensor housing having a cavity, the sensor being disposed within the cavity of the sensor housing; and (b) an electronics module, said electronics module comprising (i) an electronics housing, the electronics housing having a cavity, (ii) a multi-potentiostat disposed within the cavity of the electronics housing, the multi-potentiostat being coupled to the sensor so as to simultaneously and independently control at least two of the sensing electrodes; (c) wherein one of the electronics module and the sensor module is positioned over the other.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF THE INVENTION

One innovation behind the present multi-gas microsensor assembly (multi-electrode electrochemical microsensor cell with integrated potentiostatic control and signal processing circuit) for the simultaneous detection of different gases, such as carbon dioxide and oxygen, in real time for applications in the environmental, medical, agricultural, bio-related, food, safety and security industries is the fabrication of an electrochemical microsensor module that combines an electrochemical microsensor cell substrate with a multi-potentiostat.

The microsensor cell structure may comprise two sensing electrodes (one for carbon dioxide and for oxygen) sharing a single counter electrode and a single reference electrode screen printed on a non-conductive substrate, with all of the electrodes in intimate contact with the same side of an ion-exchange solid-polymer electrolyte. The electrodes may be screen printed from noble metal inks such as gold, platinum, silver and metal oxides. Preferably, the sensor comprises a metal oxide (i.e. Ru, Ir oxide and combinations thereof) sensing electrode (for carbon dioxide) and a gold sensing electrode (for oxygen), a silver counter electrode, a silver/silver chloride reference electrode, and an anion-exchange solid-polymer electrolyte membrane in its chloride ion form in intimate contact with all of the electrodes. Using a bi-potentiostat, a constant potential may be applied between each of the two sensing electrodes and the reference electrode. The applied potential to each of the two sensing electrodes may be independently controlled by the bi-potentiostat. At this applied potential to each of the sensing electrodes, a constant current, proportional to concentration of carbon dioxide and oxygen, flows between each of the two sensing electrodes and the counter electrode. This constant current flowing between the carbon dioxide sensing electrode and the counter electrode is proportional to the concentration of the measured carbon dioxide. Similarly, the constant current flowing between the oxygen sensing electrode and the counter electrode is proportional to the concentration of measured oxygen.

In a preferred embodiment of this invention, the microsensor cell and the bi-potentiostat may be assembled in a modular format. The microsensor cell, anion-exchange membrane and associated gas access ports may be confined in a microsensor cell module, and the bi-potentiostat and associated control and data processing circuitry may be assembled in an electronics module.

Figure 1:
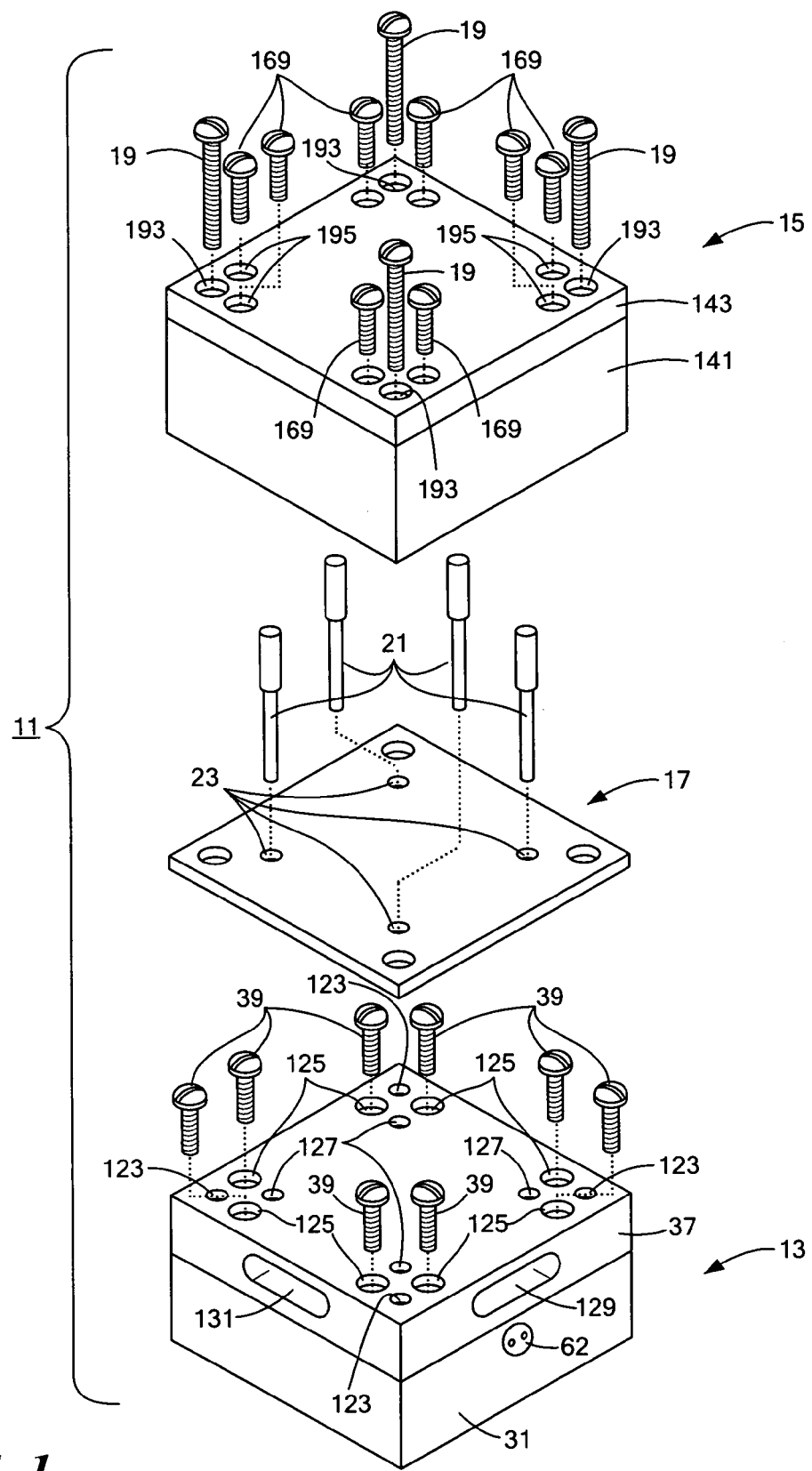
FIG. 1 is a partially exploded perspective view of one embodiment of a multi-gas microsensor assembly constructed according to the teachings of the present invention.

Referring now to FIG. 1, there is shown a partially exploded perspective view of one embodiment of a multi-gas microsensor assembly constructed according to the teachings of the present invention, said multi-gas microsensor assembly being represented generally by reference numeral 11.

Assembly 11 may comprise a sensor module 13, an electronics module 15, and a gasket 17, all of which may have matching footprints. Gasket 17 may be stacked directly on top of sensor module 13, and electronics module 15 may be stacked directly on top of gasket 17. Four screws 19 may be used to maintain sensor module 13, gasket 17, and electronics module 15 in a stacked configuration, screws 19 extending through corresponding corner holes in sensor module 13, gasket 17, and electronics module 15. In addition, as will be discussed further below, assembly 11 may also comprise a plurality of spring-loaded, electrically-conductive pins 21, pins 21 serving to electrically couple the electrodes located within sensor module 13 to a bi-potentiostat located within electronics module 15 while, at the same time, keeping each of sensor module 13 and electronics module 15 in intimate contact with gasket 17. Openings 23 may be provided in gasket 17 to receive pins 21.

Figure 2B:
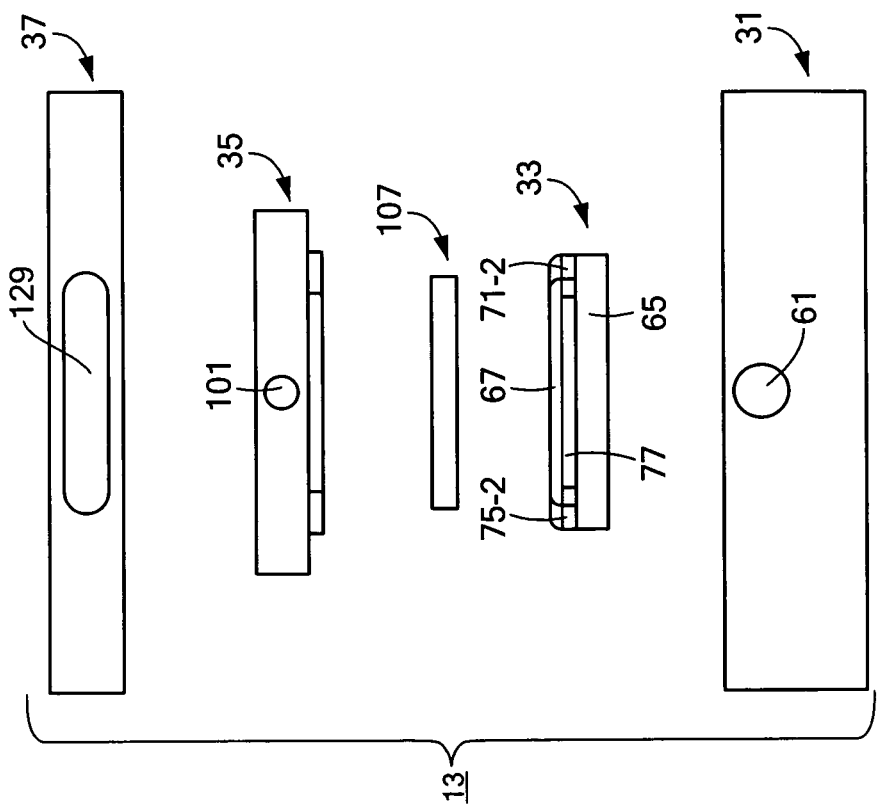
FIGS. 2(a) and 2(b) are perspective and partially exploded front views, respectively, of the sensor module shown in FIG. 1, the sensor module screws and the water plug not being shown in FIG. 2(b) for the sake of simplicity.
Figure 2A:
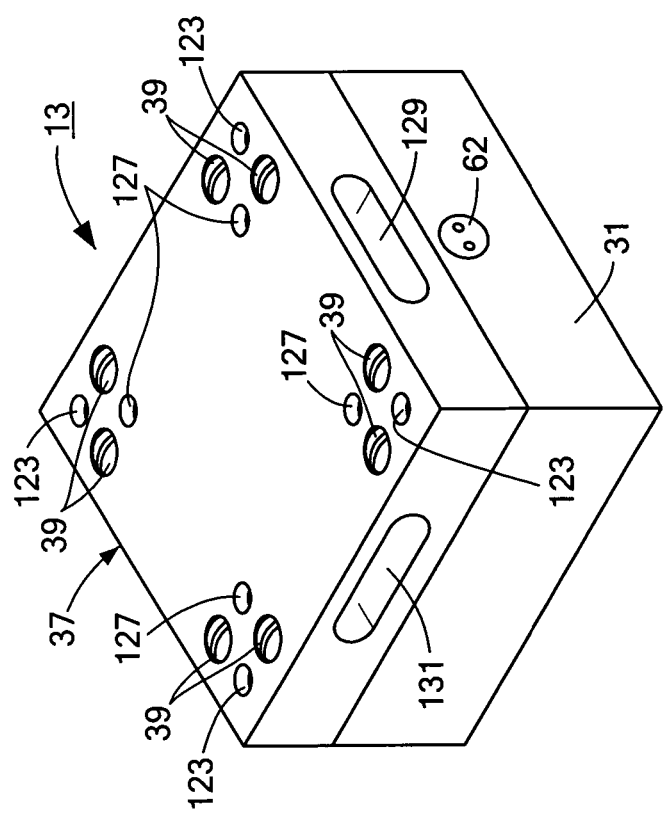
Figure 3A:
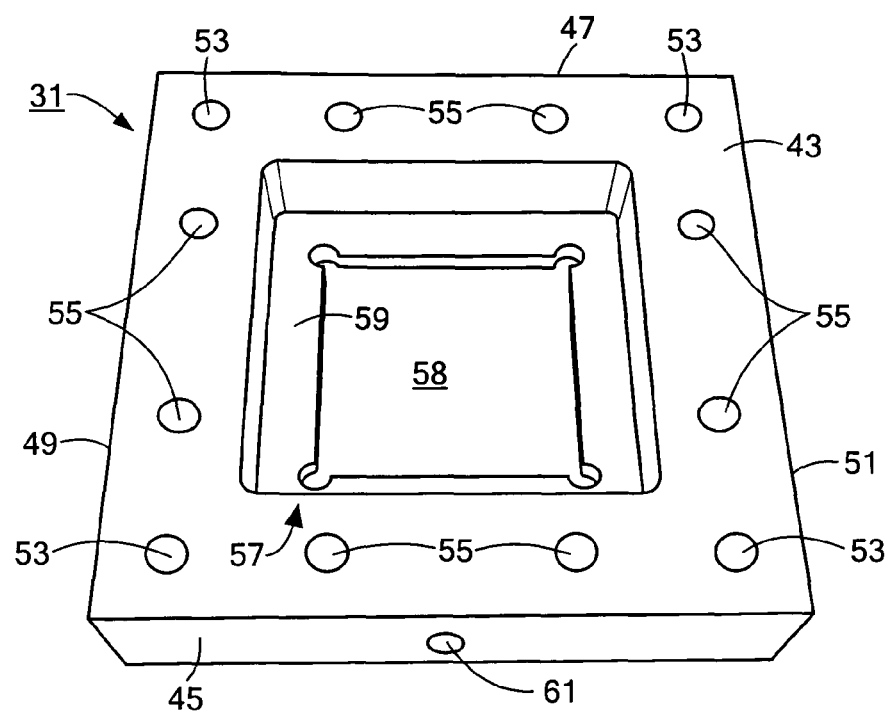
FIGS. 3(a) through 3(d) are perspective, top, bottom, and front views, respectively, of the base portion of the sensor module shown in FIG. 2(b)
Figure 3B:
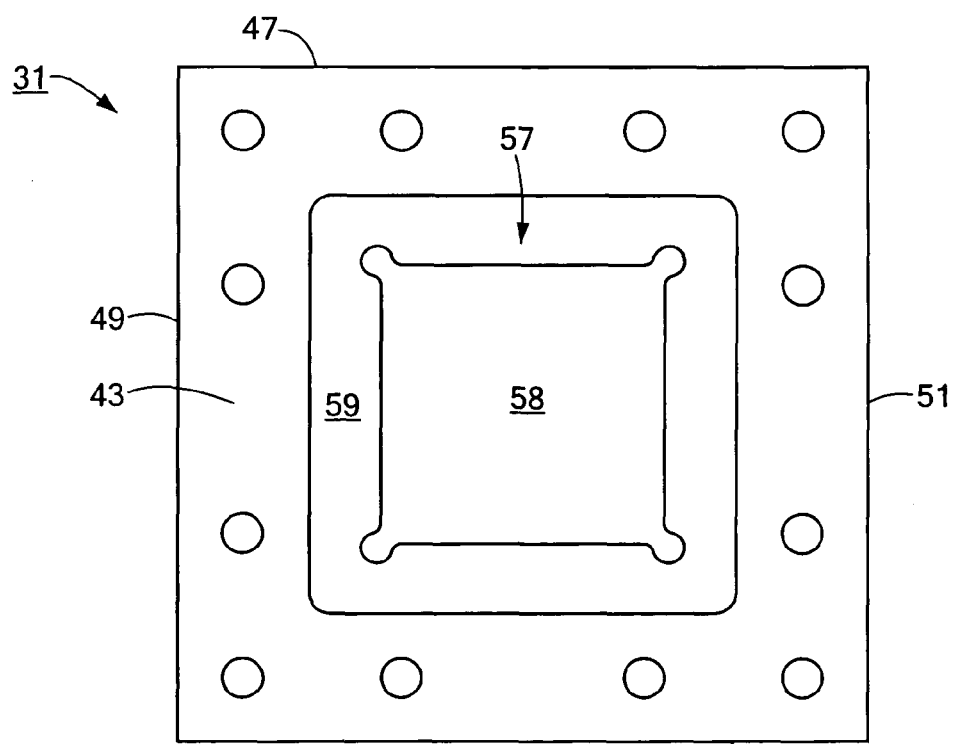
Figure 3C:
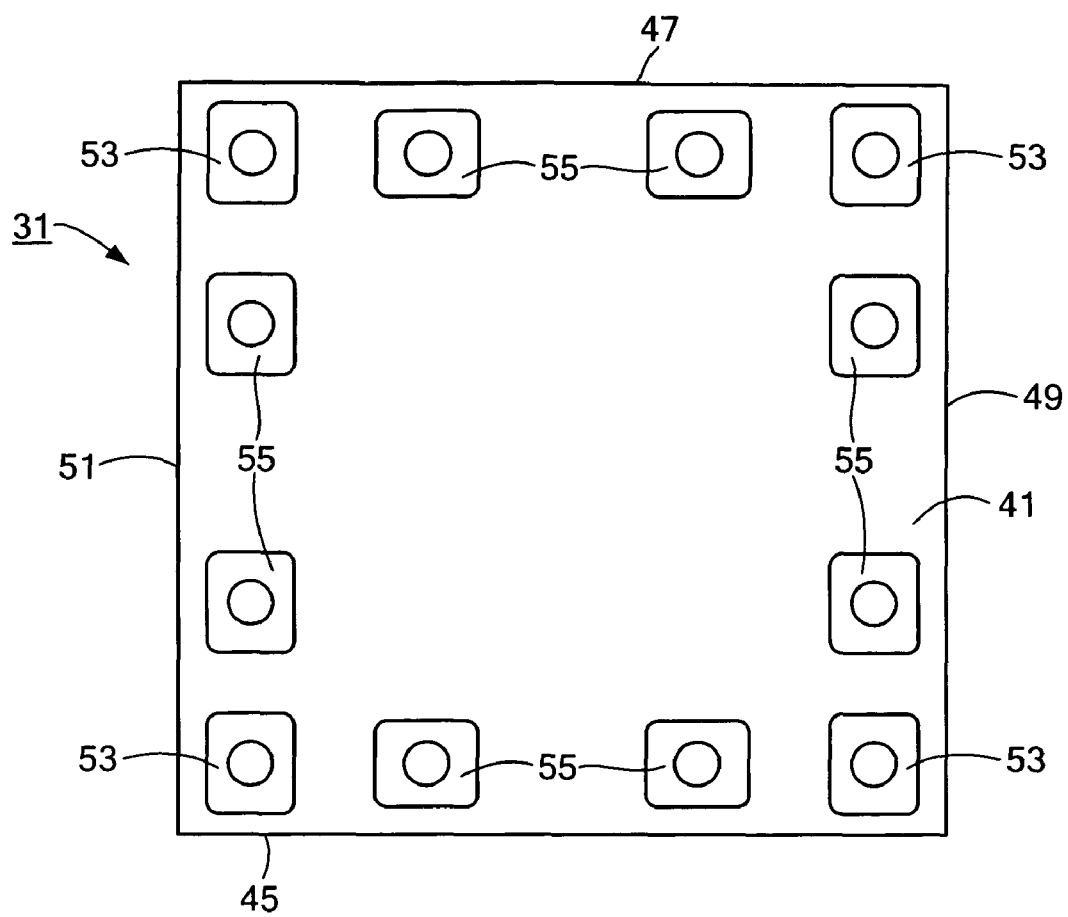
Figure 3D:
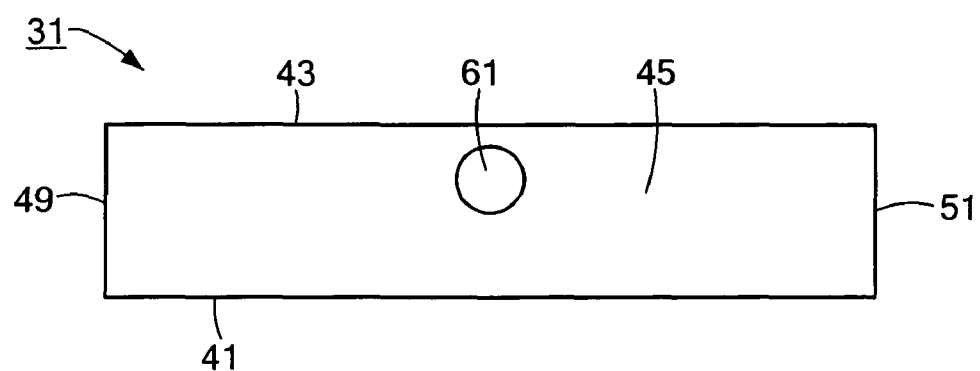

Referring now to FIGS. 2(a) and 2(b), sensor module 13 may be seen in greater detail. Sensor module 13 may comprise a base 31, a sensor 33, an inner tray 35, and a cover 37. In addition, sensor module 13 may comprise a plurality of screws 39 for securing cover 37 to base 31.

Base 31, which is also shown separately in FIGS. 3(a) through 3(d), may be a chemically-inert, electrically-non-conductive, rigid, one-piece structure, made, for example, from a suitably molded plastic. Base 31 may be a generally rectangular prismatic block shaped to include a bottom 41, a top 43, a front 45, a rear 47, a left side 49, and a right side 51. A plurality of openings 53 for receiving screws 19 may be provided in base 31, openings 53 extending from top 43 to bottom 41 proximate to the respective corners of base 31, the upper portions of openings 53 having a circular shape and a comparatively smaller diameter, the lower portions of openings 53 having a rectangular shape and a comparatively larger diameter. A plurality of openings 55 for receiving screws 39 may be provided in base 31, openings 55 extending from top 43 to bottom 41 and being located between openings 53 proximate to the periphery of base 31, the upper portions of openings 55 having a circular shape and a comparatively smaller diameter, the lower portions of openings 55 having a rectangular shape and a comparatively larger diameter. A central recess 57 may be provided in base 31, recess 57 extending downwardly from top 43 in the direction of, but not passing through, bottom 41. Central recess 57, in turn, may include a lower shelf 58 of generally square shape and comparatively smaller size and an upper shelf 59 of generally square shape and comparatively larger size. As will be discussed further below, lower shelf 58 may be appropriately dimensioned to matingly receive sensor 33, and upper shelf 59 may be appropriately dimensioned to matingly receive inner tray 35. A fluid channel 61 may be provided in base 31, channel 61 extending from front 45 to central recess 57. As will be discussed further below, channel 61 may be used to supply water to inner tray 35. A screw or plug 62 (see FIGS. 1 and 2(a)) may be removably mounted within the outer end of channel 61 to prevent the undesired flow of water therethrough.

Figure 4A:
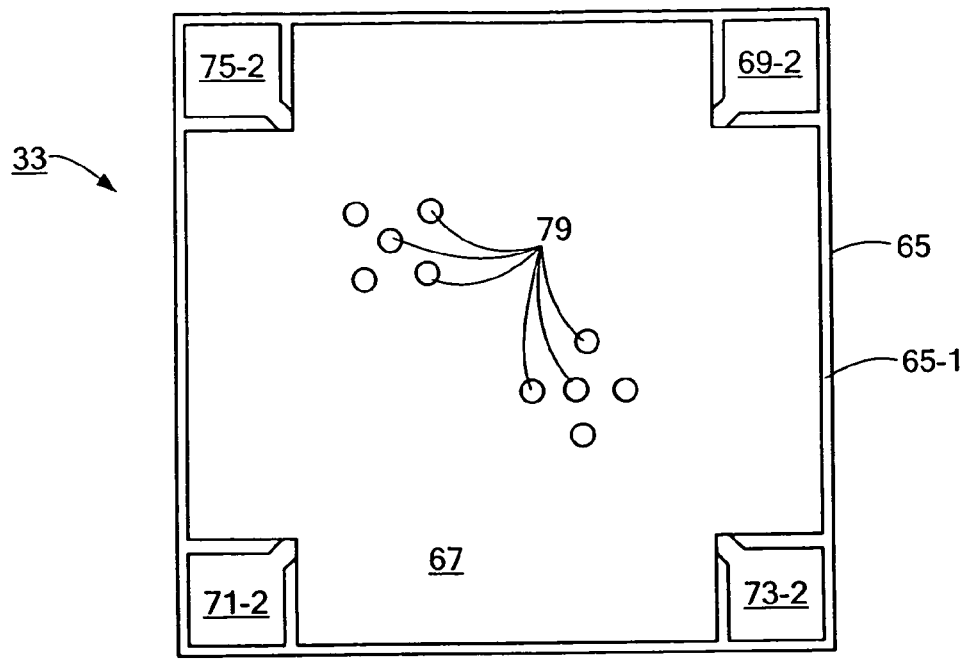
FIGS. 4(a) through 4(c) are top views of the sensor shown in FIG. 2(b), with the solid polymer electrolyte not being shown in FIG. 4(b), and with the solid polymer electrolyte and the insulator not being shown in FIG. 4(c)
Figure 4B:
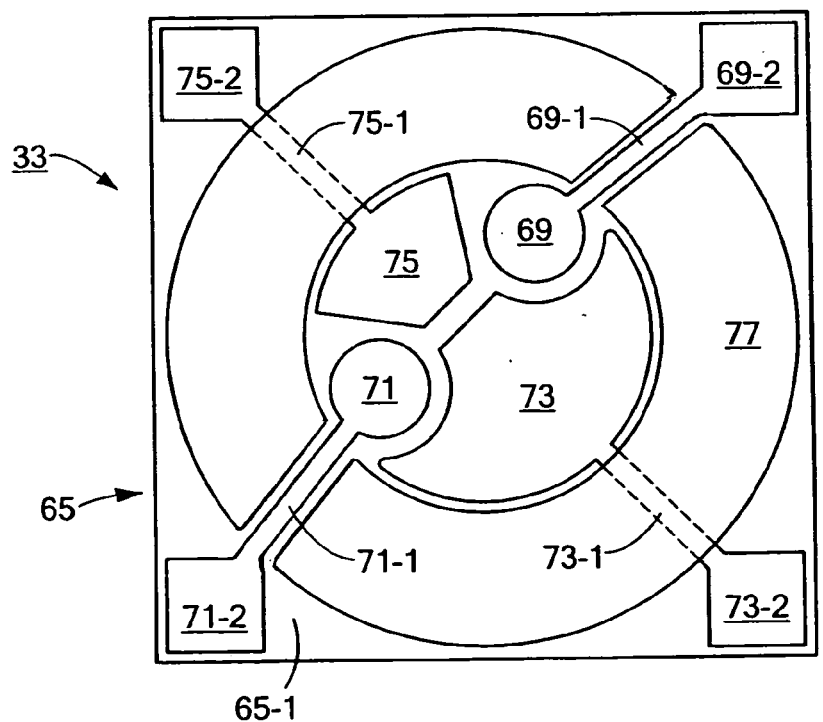
Figure 4C:
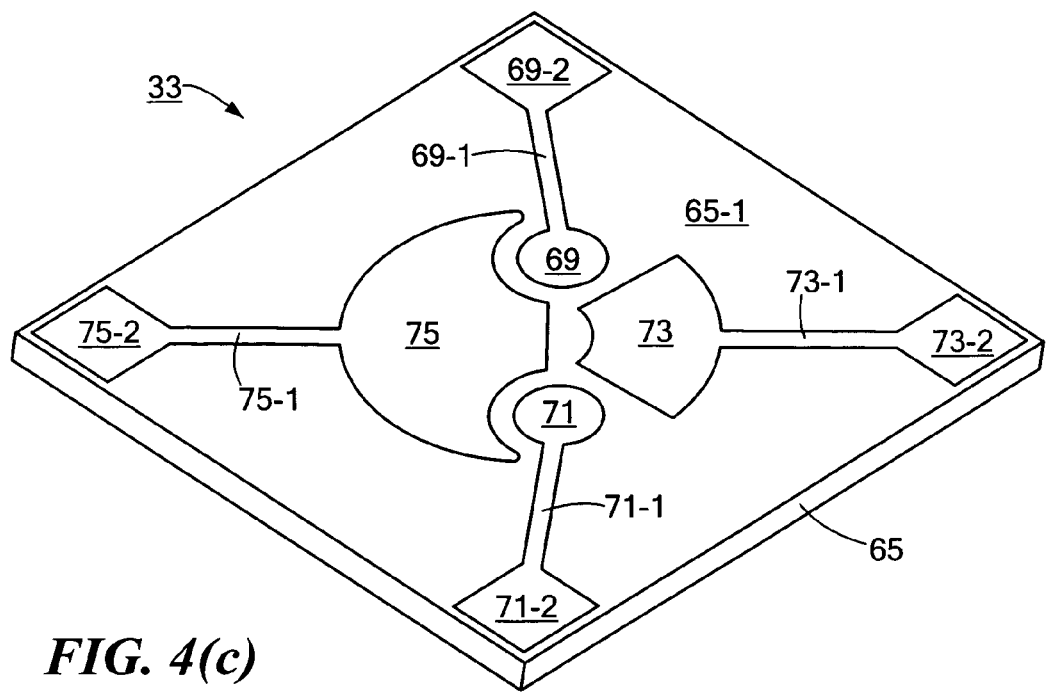
Figure 5A:
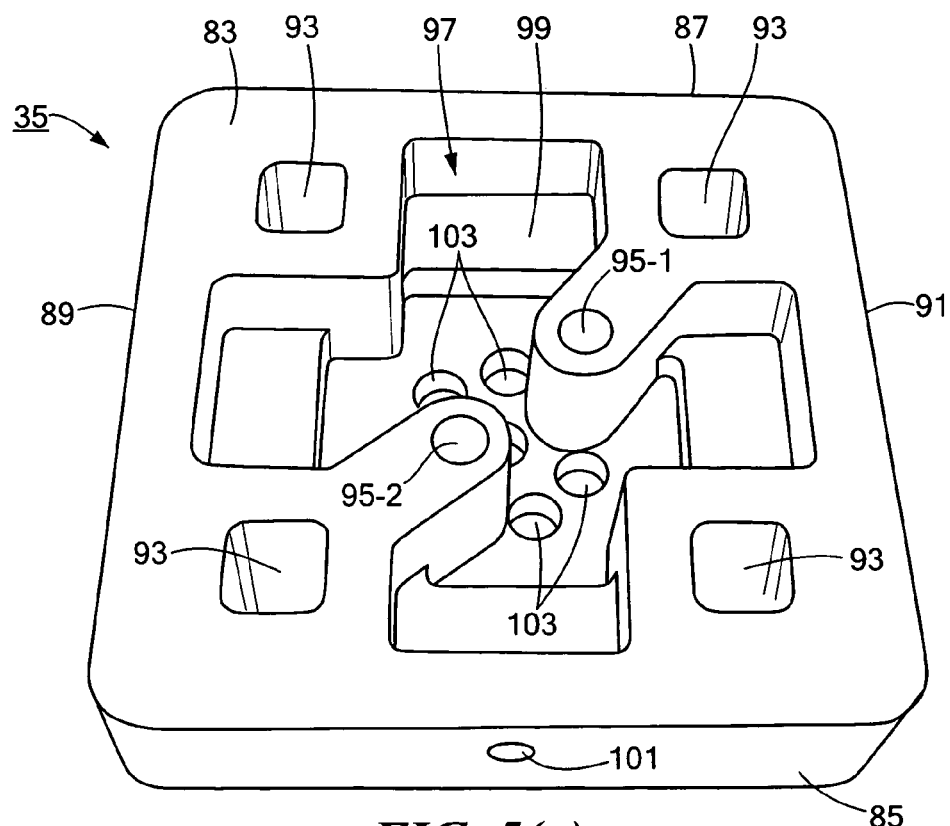
FIGS. 5(a) through 5(d) are perspective, top, bottom, and front views, respectively, of the inner tray of the sensor module shown in FIG. 2(b)
Figure 5B:
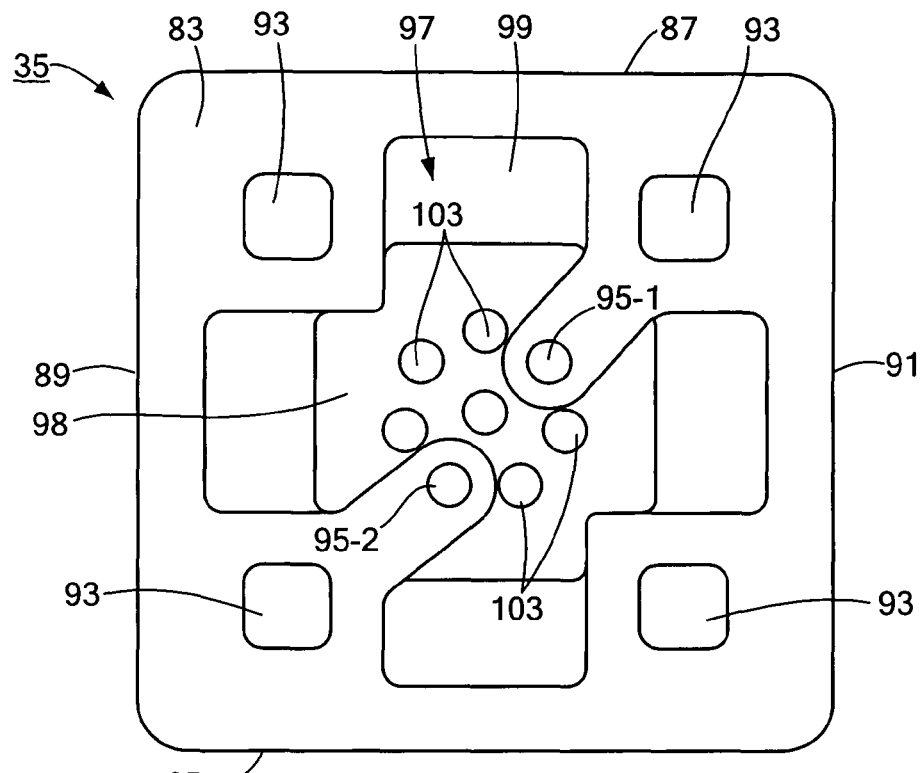
Figure 5C:
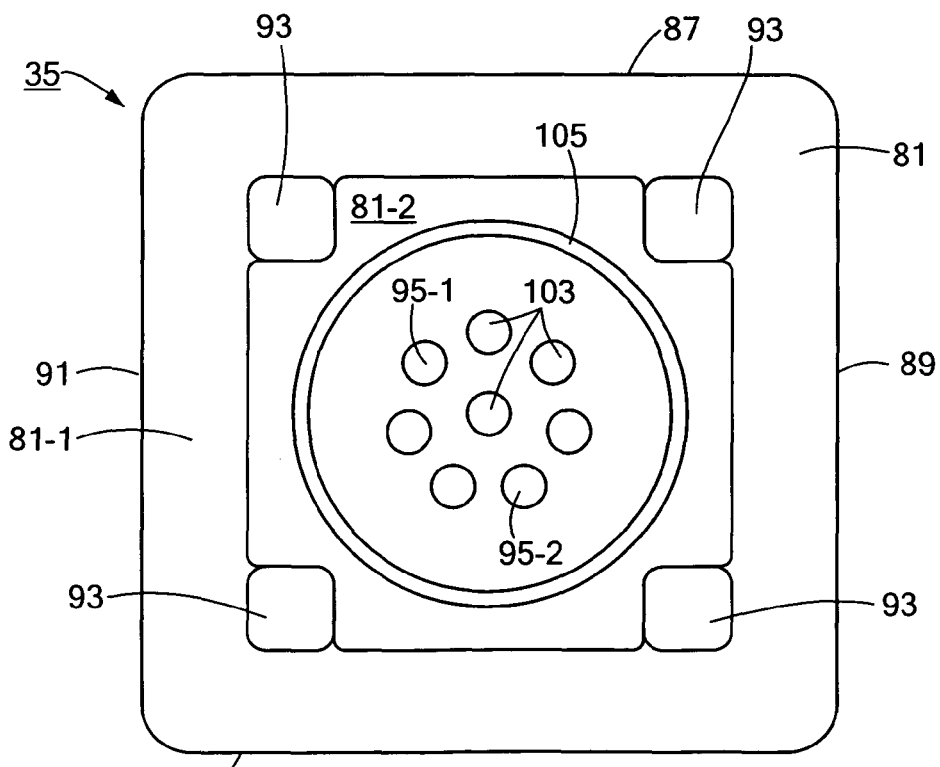
Figure 5D:
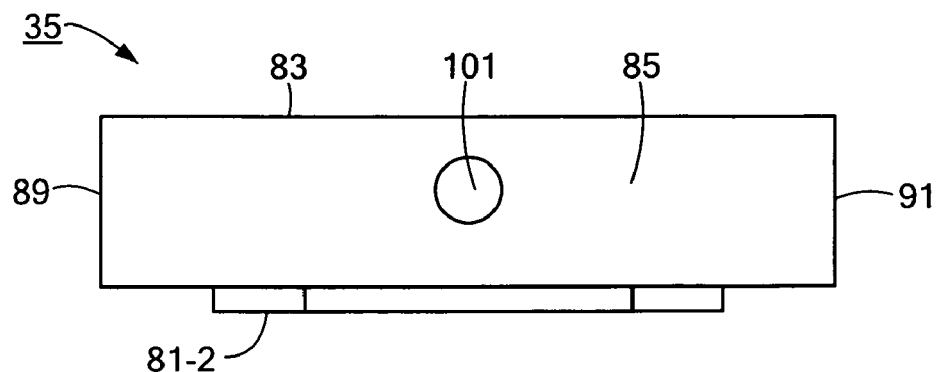

Sensor 33, which is also shown separately in FIGS. 4(a) through 4(c), may be removably seated on lower shelf 58 and may comprise a non-conductive solid substrate 65, a plurality of electrodes positioned over and in intimate contact with solid substrate 65, and a solid polymer electrolyte ion-exchange membrane 67 positioned over and in intimate contact with both the plurality of electrodes and the exposed areas of solid substrate 65.

Solid substrate 65, which may be a one-piece, generally rectangular, prismatic structure having a top surface 65-1 of generally square shape, may be made of one or more of the following: inorganic materials, such as alumina, silica and titania, and organic polymers or plastics, including polyesters, polyimides, polysulfones, polyethers, polystyrenes, polyethylenes, polypropylenes, polycarbonates, and liquid crystal polymers.

The plurality of electrodes on solid substrate 65 may include a first sensing electrode 69, a second sensing electrode 71, a counter electrode 73, and a reference electrode 75, with first sensing electrode 69 and second sensing electrode 71 sharing each of counter electrode 73 and reference electrode 75. Where, as in the present embodiment, sensor 33 is designed to detect carbon dioxide gas and oxygen gas, first sensing electrode 69 may be a carbon dioxide sensing electrode and may comprise, for example, an electrochemically reversible metal oxide (e.g., $M_2O_3$ or $MO_2$), such as ruthenium oxide, iridium oxide, or a combination thereof; second sensing electrode 71 may be an oxygen sensing electrode and may comprise, for example, gold; counter electrode 73 may comprise, for example, silver or platinum/air ($O_2$); and reference electrode 75 may comprise, for example, silver/silver chloride or platinum/air ($O_2$). The aforementioned electrodes may be screen printed or deposited thermally or electrochemically on solid substrate 65 in a planar three-electrode configuration. First sensing electrode 69, second sensing electrode 71, counter electrode 73 and reference electrode 75 may be arranged in a substantially circular pattern on top surface 65-1 of solid substrate 65, with first sensing electrode 69 being connected by a generally radially-extending lead 69-1 to a contact pad 69-2 located at a first corner of top surface 65-1, second sensing electrode 71 being connected by a generally radially-extending lead 71-1 to a contact pad 71-2 located at a second corner of top surface 65-1, counter electrode 73 being connected by a generally radially-extending lead 73-1 to a contact pad 73-2 located at a third corner of top surface 65-1, and reference electrode 75 being connected by a generally radially-extending lead 75-1 to a contact pad 75-2 located at a fourth corner of top surface 65-1.

An electrical insulator 77 of generally annular shape may be included in sensor 33, insulator 77 being screen printed or otherwise deposited on top surface 65-1 of substrate 65 at a location disposed radially outwardly relative to electrodes 69, 71, 73 and 75 and radially inwardly relative to contact pads 69-2, 71-2, 73-2 and 75-2, with insulator 77 covering leads 73-1 and 75-2 but not covering leads 69-1 and 71-1.

Where, as noted above, sensor 33 is used to detect carbon dioxide gas and oxygen gas using, for example, metal oxide and gold sensing electrodes, respectively, solid polymer electrolyte ion-exchange membrane 67 may be a solid polymer electrolyte anion exchange membrane. Such a solid polymer electrolyte anion exchange membrane may be a quaternary ammonium ion anion exchange polymer or ionomer in the chloride, carbonate, bicarbonate, or sulfate ion form. By contrast, where sensor 33 is used to detect, instead of carbon dioxide gas, alkaline gases, such as ammonia ($NH_3$) and hydrazines (e.g., hydrazine ($NH_2NH_2$), monomethyl hydrazine ($CH_3NHNH_2$), and asymmetrical dimethyl hydrazine (($CH_3)_2NHNH_2$)), a solid polymer electrolyte cation exchange membrane may be used.

Membrane 67 may be generally dimensioned to correspond to the footprint of substrate 65, except that the corners of membrane 67 may be removed to expose contact pads 69-2, 71-2, 73-2, and 75-2. In addition, a plurality of openings 79 serving as gas diffusion ports to the sensing electrodes may be provided in membrane 67, with all of openings 79 being positioned over sensing electrodes 69 and 71, with at least one of openings 79 being positioned over sensing electrode 69 and at least one of openings 79 being positioned over electrode 71. Openings 79, which may take any of a variety of shapes, such as circular, rectangular, and oval (e.g., slits), preferably each have a footprint entirely within that of the underlying sensing electrode so as to form, upon the diffusion of gas through the opening, an electrochemically active gas/electrode/membrane interface. As can be appreciated, by increasing the number and/or size of openings 79 positioned over a sensing electrode, one may increase the size of said interface and, therefore, may increase sensitivity of the sensor to the gas being detected. In addition, one may further enhance the sensitivity of the sensor by pouring, in liquid form, the same or similar type of material used to make membrane 67 into openings 79 and allowing said material to solidify, whereby a multitude of cracks or pores may be formed that may be used to make the aforementioned interfaces.

It is to be understood that, although sensor 33 is shown having two sensing electrodes, sensor 33 could include three or more (i.e., as many as eight or possibly more) sensing electrodes.

Inner tray 35, which is also shown separately in FIGS. 5(a) through 5(d), may comprise a chemically-inert, electrically-non-conductive, rigid, one-piece structure, made, for example, from a suitably molded plastic. Tray 35 may be a generally rectangular prismatic block shaped to include a bottom 81, a top 83, a front 85, a rear 87, a left side 89, and a right side 91. Bottom 81 may be shaped to include a peripheral portion 81-1 and a central portion 81-2, central portion 81-2 extending downwardly past peripheral portion 81-1 by a short distance. As noted above, tray 35 may be removably mated with central recess 57 so that top 83 of tray 35 lies flush with top 43 of base 31 and so that peripheral portion 81-1 of tray 35 sits directly on top of upper shelf 59, with central portion 81-2 of tray 35 extending downwardly from upper shelf 59 to keep sensor 33 stationary against lower shelf 58. A plurality of openings 93 alignable with contact pads 69-2, 71-2, 73-2 and 75-2 of sensor 33 and adapted to receive pins 21 may be provided in tray 35, openings 93 extending from top 83 to bottom 81 proximate to the respective corners of tray 35. A pair of openings 95-1 and 95-2 alignable with sensing electrodes 69 and 71, respectively, for delivering the gases to be detected to electrodes 69 and 71 may be provided in tray 35, openings 95-1 and 95-2 extending from top 83 to bottom 81 of tray 35. A central recess 97 may be provided in tray 35, recess 97 extending downwardly from top 83 in the direction of, but not passing through, bottom 81. Central recess 97, in turn, may include a lower shelf 98 of generally square shape and comparatively smaller size and an upper shelf 99 of generally "+"-shape and comparatively larger size. A fluid channel 101 may be provided in tray 35, channel 101 extending from front 85 to central recess 97 and being alignable with channel 61 of base 31. (Screw or plug 62 may extend into channel 101 to prevent the escape of water from tray 35 into base 31 and to immobilize tray 35 relative to base 31.) In addition, a plurality of fluid pores 103 may extend transversely through lower shelf 98, pores 103 being alignable with the top surface of membrane 67. In this manner, water may be delivered to central recess 97 through channel 61 of base 31 and through channel 101 of tray 35 and, thereafter, may be delivered to membrane 67 through pores 103. In this manner, membrane 67 may be kept in a properly humidified state.

A circular groove 105 circumscribing pores 103, as well as openings 95-1 and 95-2, may be provided on the bottom surface of central portion 81-2 of tray 35. Groove 105 may receive an O-ring 107 for forming a fluid seal on membrane 67. In this manner, water delivered to membrane 67 through pores 103 is kept away from contact pads 69-2, 71-2, 73-2 and 75-2.

Figure 6A:
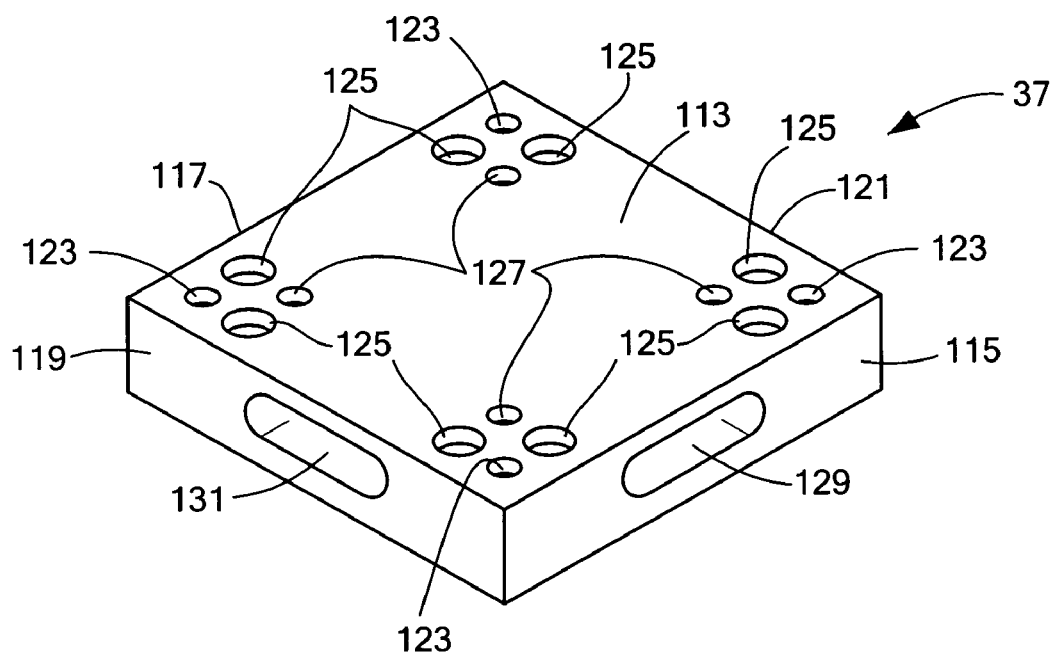
FIGS. 6(a) and 6(b) are perspective and bottom views, respectively, of the cover of the sensor module shown in FIG. 2(b)
Figure 6B:
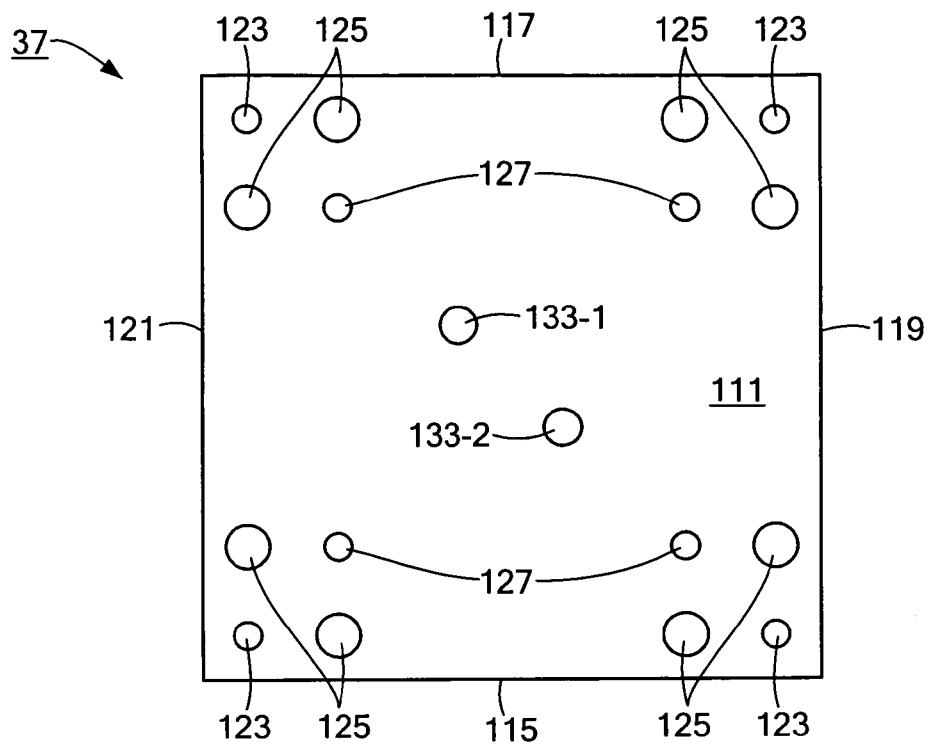

Cover 37, which is also shown separately in FIGS. 6(a) and 6(b), may be a chemically-inert, electrically-non-conductive, rigid, one-piece structure, made, for example, from a suitably molded plastic. Cover 37, which may be sized to match the footprint of base 31 (upon which cover 37 may be seated), may be a generally rectangular prismatic block shaped to include a bottom 111, a top 113, a front 115, a rear 117, a left side 119, and a right side 121. A first plurality of transverse openings 123 may be provided in cover 37, openings 123 extending from top 113 to bottom 111 proximate to the respective corners of cover 37. Openings 123, which may be aligned with openings 53 of base 31, may be used to receive screws 19. A second plurality of transverse openings 125 may be provided in cover 37, openings 125 extending from top 113 to bottom 111 between openings 123 and proximate to the periphery of cover 37. Openings 125, which may be aligned with openings 55 of base 31, may be used to receive screws 39. A third plurality of transverse openings 127 may be provided in cover 37. Openings 127, which may be used to receive pins 21, may extend from top 113 to bottom 111 and may be aligned with openings 93 of tray 35.

A pair of intersecting fluid delivery channels 129 and 131 may be provided in cover 37, with channel 129 extending from front 115 to rear 117 and with channel 131 extending from left side 119 to right side 121. A pair of openings 133-1 and 133-2 may be provided in bottom 111 of cover 37, each of openings 133-1 and 133-2 being in fluid communication with each of channels 129 and 131. Opening 133-1 may be aligned with opening 95-1 of tray 35, and opening 133-2 may be aligned with opening 95-2 of tray 35. In this manner, fluid containing carbon dioxide gas and oxygen gas may enter sensor module 13 through delivery channels 129 and/or 131 and then may be delivered to electrodes 69 and 71 by passing through openings 133-1 and 133-2, and then through openings 95-1 and 95-2, respectively. The passage of fluid through channels 129 and/or 131 may be passive or may be aided with a pump or the like.

Figure 9A:
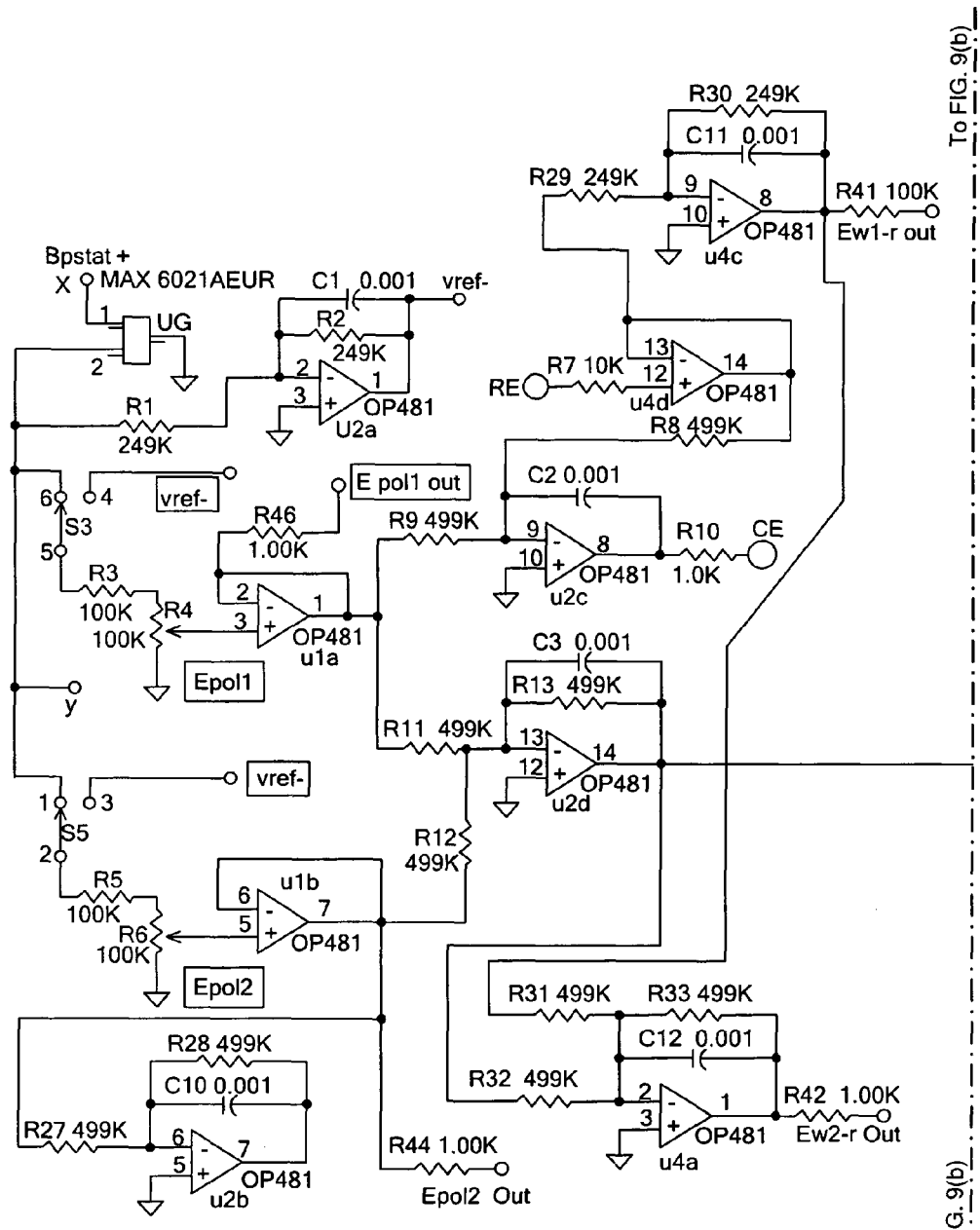
FIGS. 9(a) through 9(c) collectively represent a schematic of the bi-potentiostat used in the multi-gas microsensor assembly of FIG. 1.
Figure 9B:
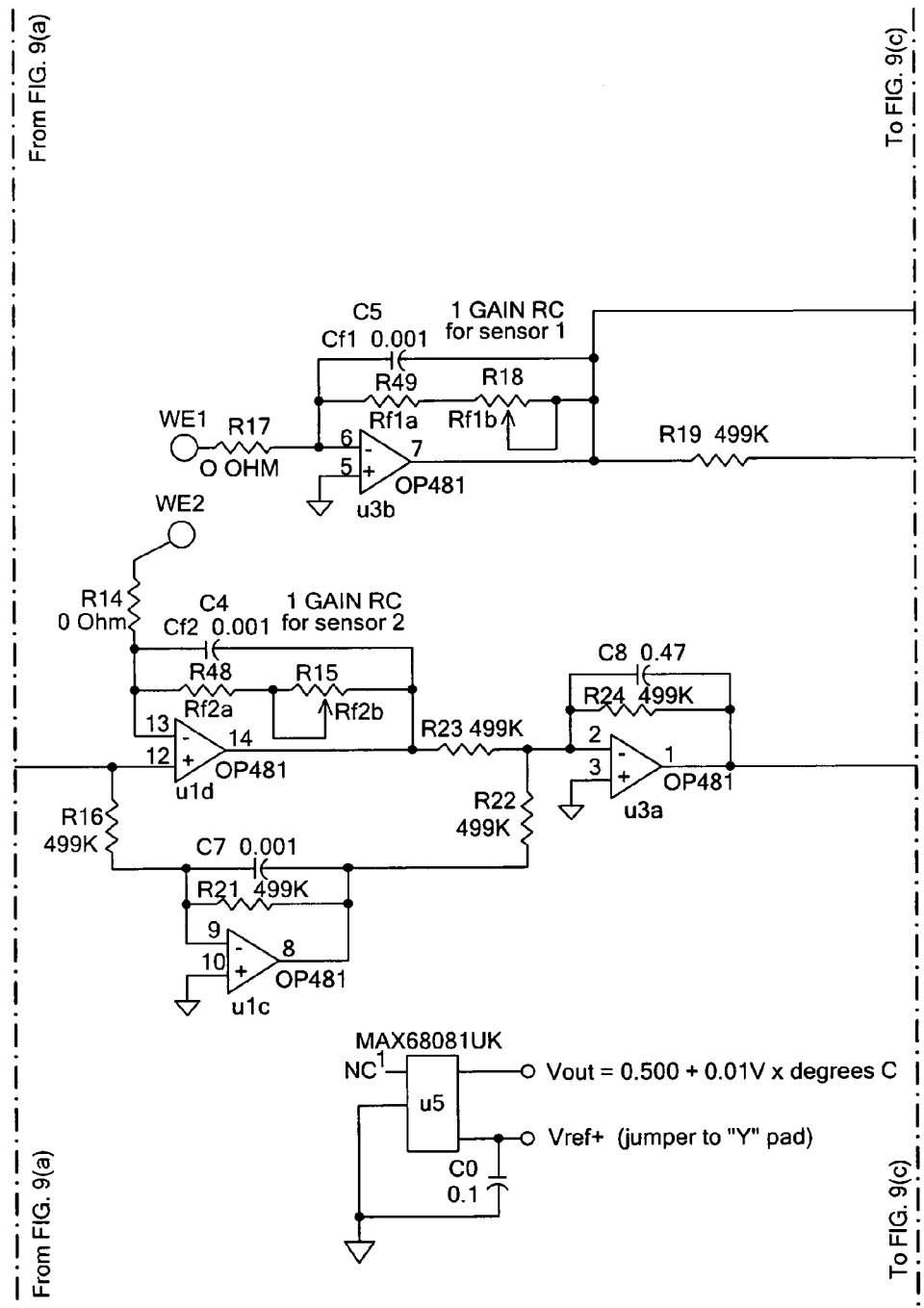
Figure 9C:
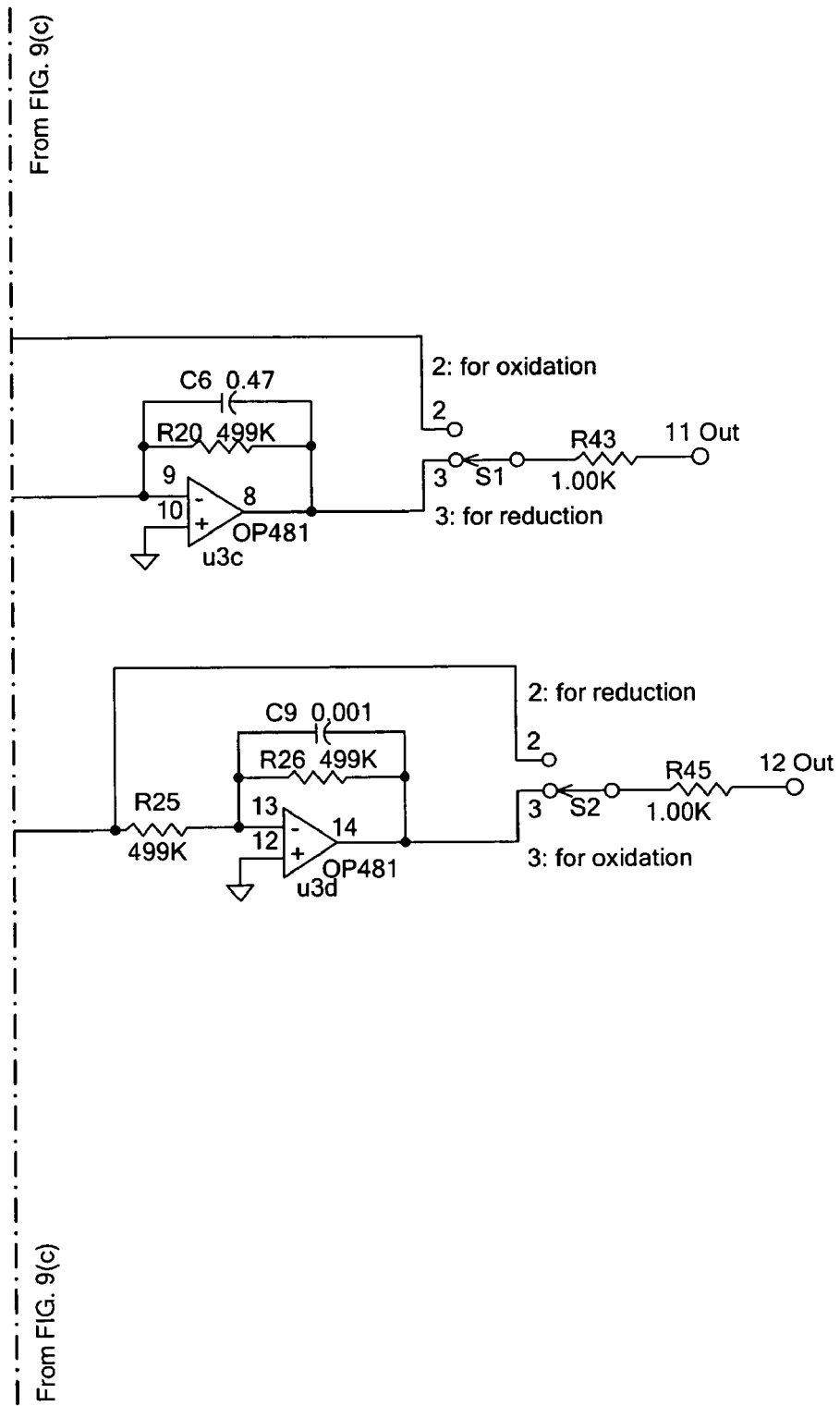

Electronics module 15 may comprise a base 141, a cover 143 removably mounted on base 141, and electronics (shown schematically FIGS. 9(a) through 9(c)) removably disposed within base 141.

Figure 7A:
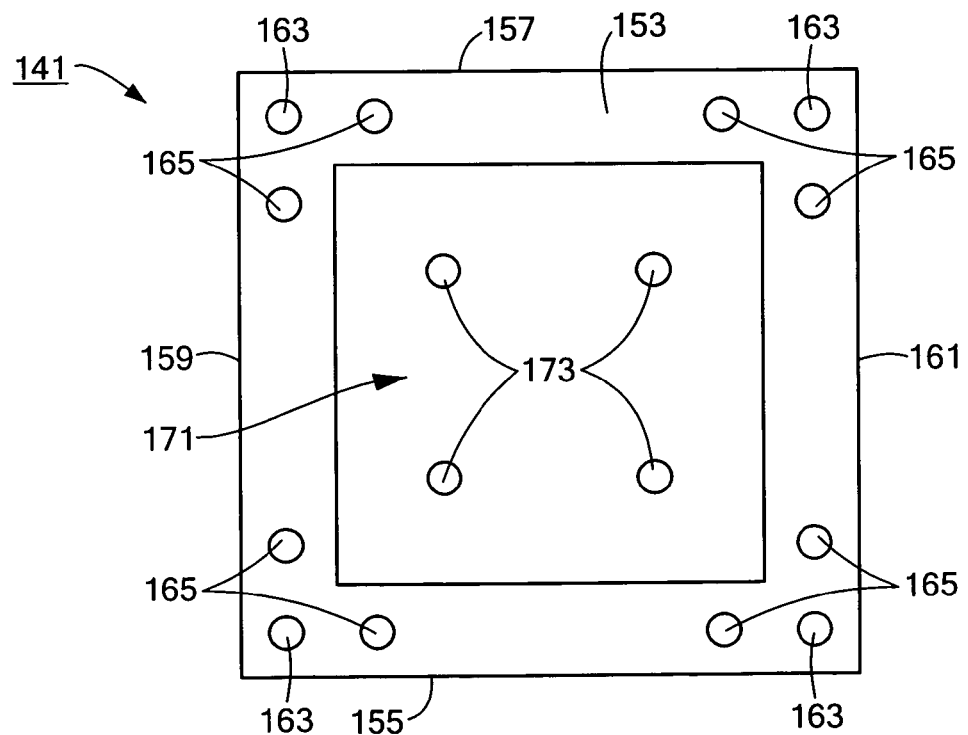
FIGS. 7(a) and 7(b) are top and bottom views, respectively, of the base of the electronics module shown in FIG. 1.
Figure 7B:
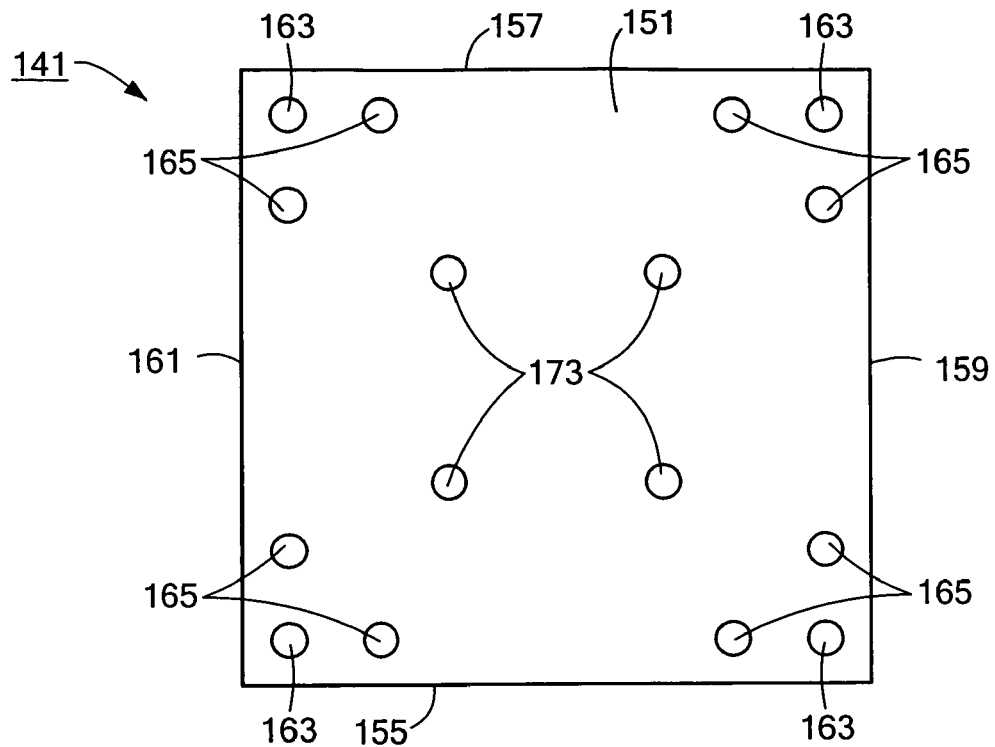

Base 141, which is also shown separately in FIGS. 7(a) and 7(b), may be a chemically-inert, electrically-non-conductive, rigid, one-piece structure, made, for example, from a suitably molded plastic. Base 141, which may be sized to match the footprint of gasket 17 (upon which base 141 may be seated), may be a generally rectangular prismatic block shaped to include a bottom 151, a top 153, a front 155, a rear 157, a left side 159, and a right side 161. A first plurality of transverse openings 163 may be provided in base 141, openings 163 extending from top 153 to bottom 151 proximate to the respective corners of base 141. Openings 163, which may be aligned with openings 123 of cover 37, may be used to receive screws 19. A second plurality of transverse openings 165 may be provided in base 141, openings 165 extending from top 153 to bottom 151 between openings 163 and proximate to the periphery of base 141. Openings 165 may be used to receive screws 169 for securing base 141 to cover 143. A central recess 171 may be provided in base 141, recess 171 extending downwardly from top 153 in the direction of, but not passing through, bottom 151. Central recess 171 may be appropriately dimensioned to receive the electronics. A plurality of transverse openings 173 may be formed in bottom 151 of base 141, openings 173 communicating with recess 171 and being adapted to receive pins 21 to electrically couple the electronics to sensors 69, 71, 73 and 75.

Figure 8A:
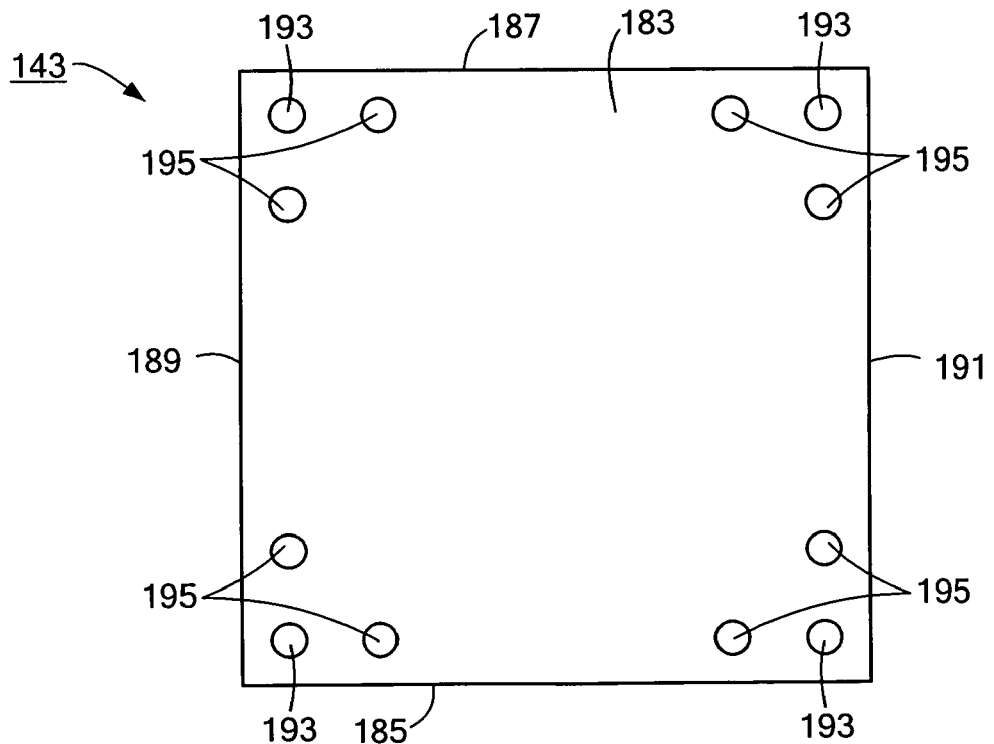
FIGS. 8(a) and 8(b) are top and bottom views, respectively, of the cover of the electronics module shown in FIG. 1.
Figure 8B:
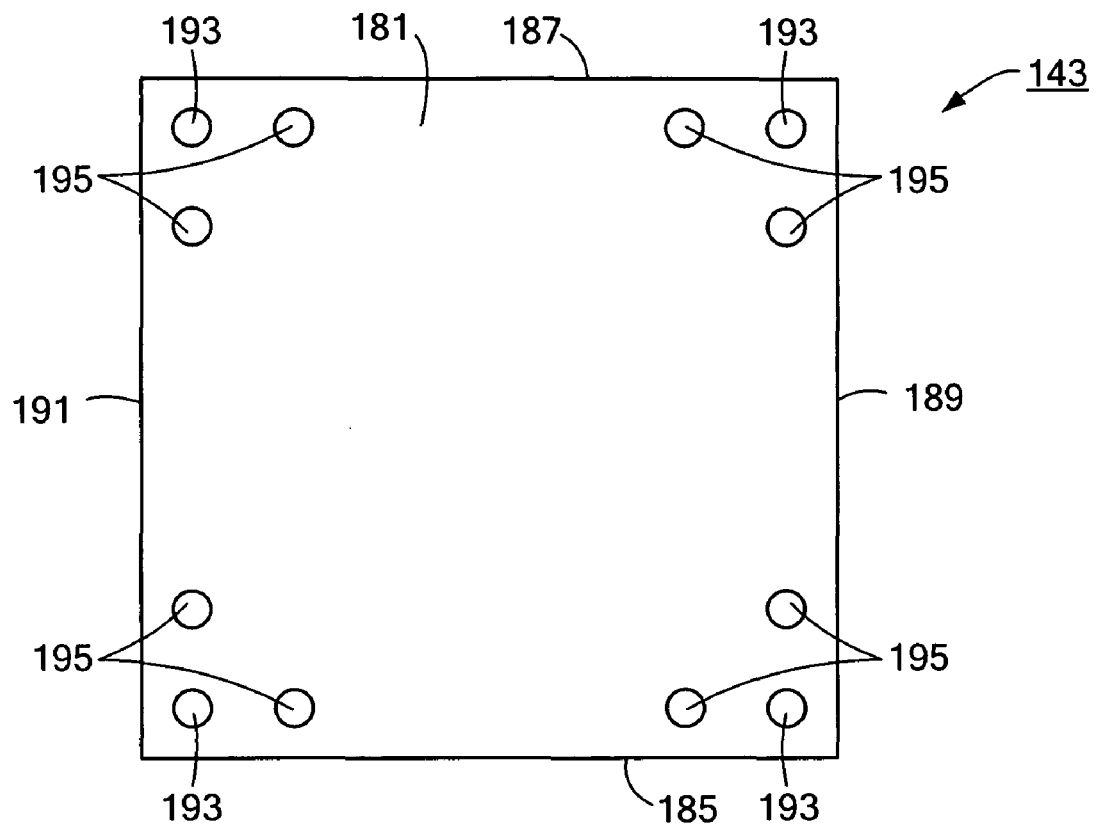

Cover 143 which is also shown separately in FIGS. 8(a) and 8(b), may be a chemically-inert, electrically-non-conductive, rigid, one-piece structure, made, for example, from a suitably molded plastic. Cover 143, which may be sized to match the footprint of base 141 (upon which cover 143 may be seated), may be a generally rectangular prismatic block shaped to include a bottom 181, a top 183, a front 185, a rear 187, a left side 189, and a right side 191. A first plurality of transverse openings 193 may be provided in cover 143, openings 193 extending from top 183 to bottom 181 proximate to the respective corners of cover 143. Openings 193, which may be aligned with openings 163 of base 141, may be used to receive screws 19. A second plurality of transverse openings 195 may be provided in cover 143, openings 195 extending from top 183 to bottom 181 between openings 193 and proximate to the periphery of cover 143. Openings 195, which may be aligned with openings 165 of base 141, may be used to receive screws 169.

The electronics received in base 141 may include a potentiostat board, as well as a signal control and transfer board and other desired components. A schematic of a bi-potentiostat circuit, which may be used to control the two sensing electrodes simultaneously and independently, is shown in FIGS. 9(a) through 9(c).

Preferably, the electronics are configured so that regeneration and reactivation of the metal oxide sensing electrode is automatically performed by oxidation through application of periodic electrical pulses to the sensing electrode, so that regeneration of the counter electrode catalyst is automatically performed by reduction through application of periodic electrical pulses, and so that restoration of the solid polymer electrolyte membrane is automatically performed by application of periodic electrical pulses, as described above, to the electrodes and catalyst.

In another embodiment (not shown), the sensing electrodes may be positioned on a first solid, non-conductive substrate, and the counter electrode and the reference electrode may be positioned on a second solid, non-conductive substrate, the various electrodes sharing a single solid polymer electrolyte ion-exchange membrane. For example, the electrodes may be in contact with the same surface of the solid polymer electrolyte ion-exchange membrane or with opposing surfaces of the solid polymer electrolyte ion-exchange membrane.

The examples below are illustrative only and do not limit the present invention.

Example 1

Simultaneous Detection of Carbon Dioxide and Oxygen in the Laboratory

Figure 10:
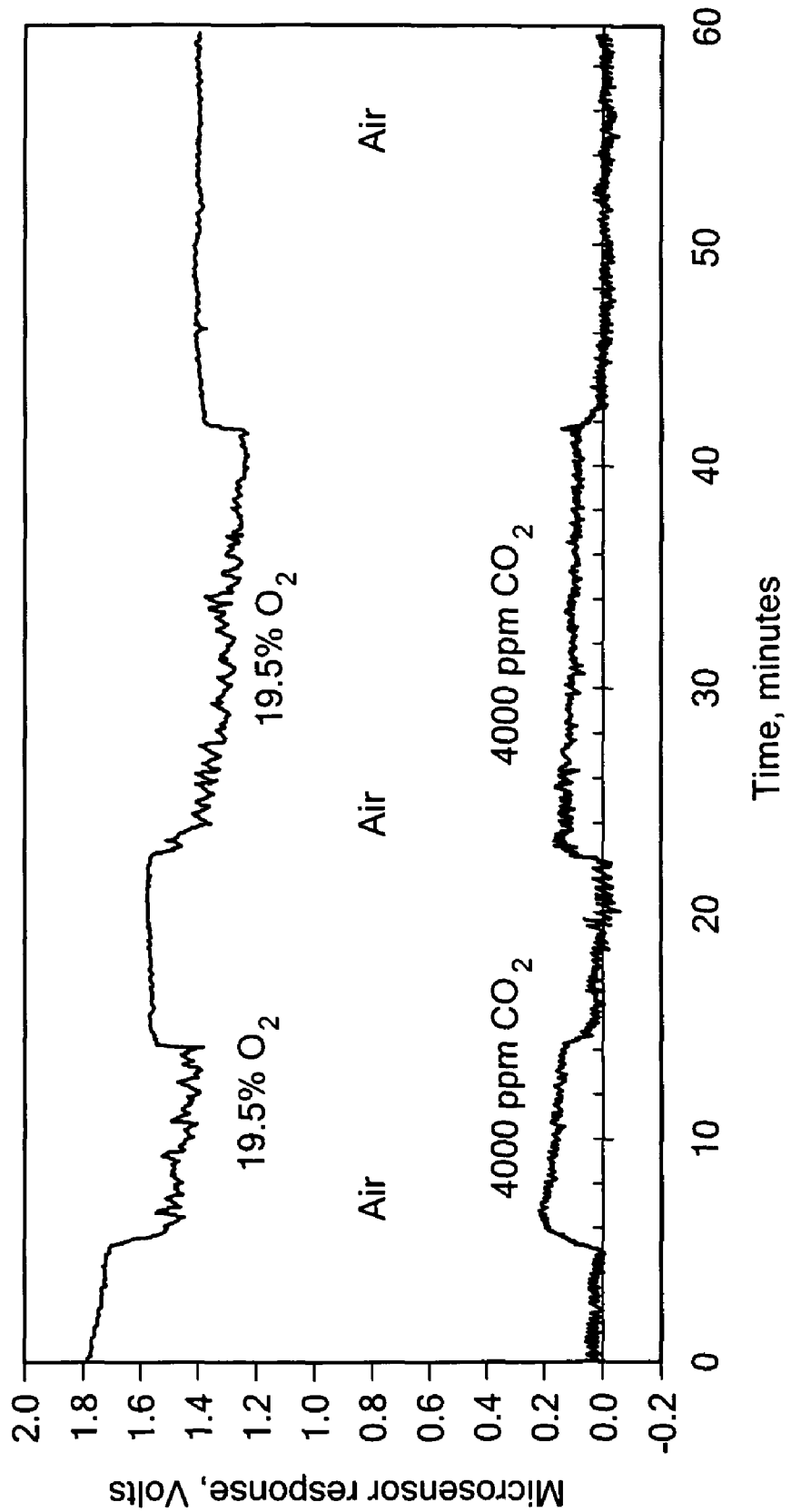
FIG. 10 depicts the response curve for the simultaneous detection of carbon dioxide and oxygen using the multi-gas microsensor assembly as described in Example 1.

A prototype multi-gas microsensor assembly similar to assembly 11 was tested in a laboratory for the simultaneous detection of carbon dioxide and oxygen gas mixtures. The assembled microsensor was placed in a plastic test container and exposed to air (21% $O_2$, 400 ppm $CO_2$) followed by a mixture of carbon dioxide/nitrogen to simulate an increase in nitrogen and concomitant decrease in the oxygen content in the plastic test container, and increase of carbon dioxide concentration. FIG. 10 shows the response curve of the microsensor assembly for simultaneous detection of carbon dioxide and oxygen concentrations.

Example 2

Simultaneous Detection of Carbon Dioxide and Oxygen in an Automobile

Figure 11A:
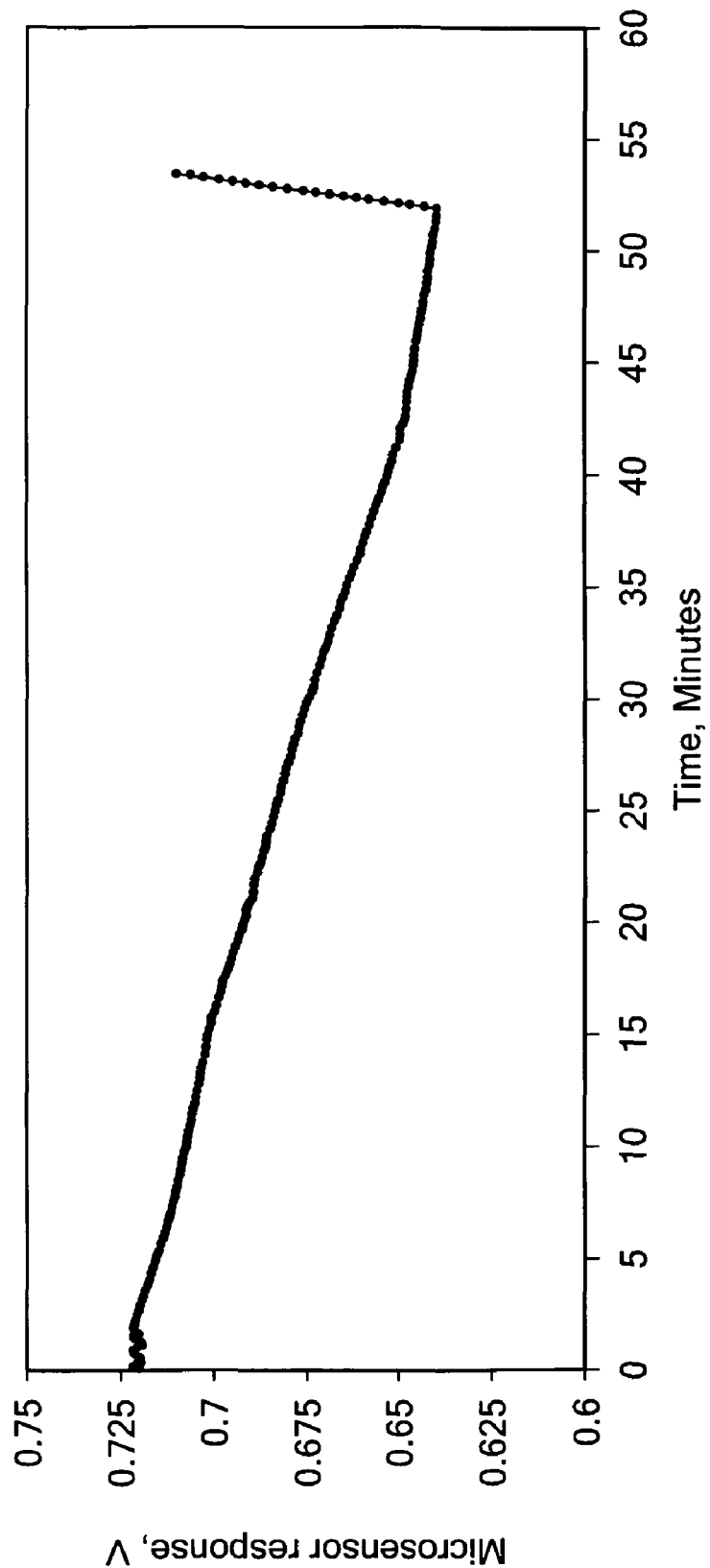
FIGS. 11(a) and 11(b) show the response curves for oxygen and carbon dioxide, respectively, using the microsensor assembly as described in Example 2.
Figure 11B:
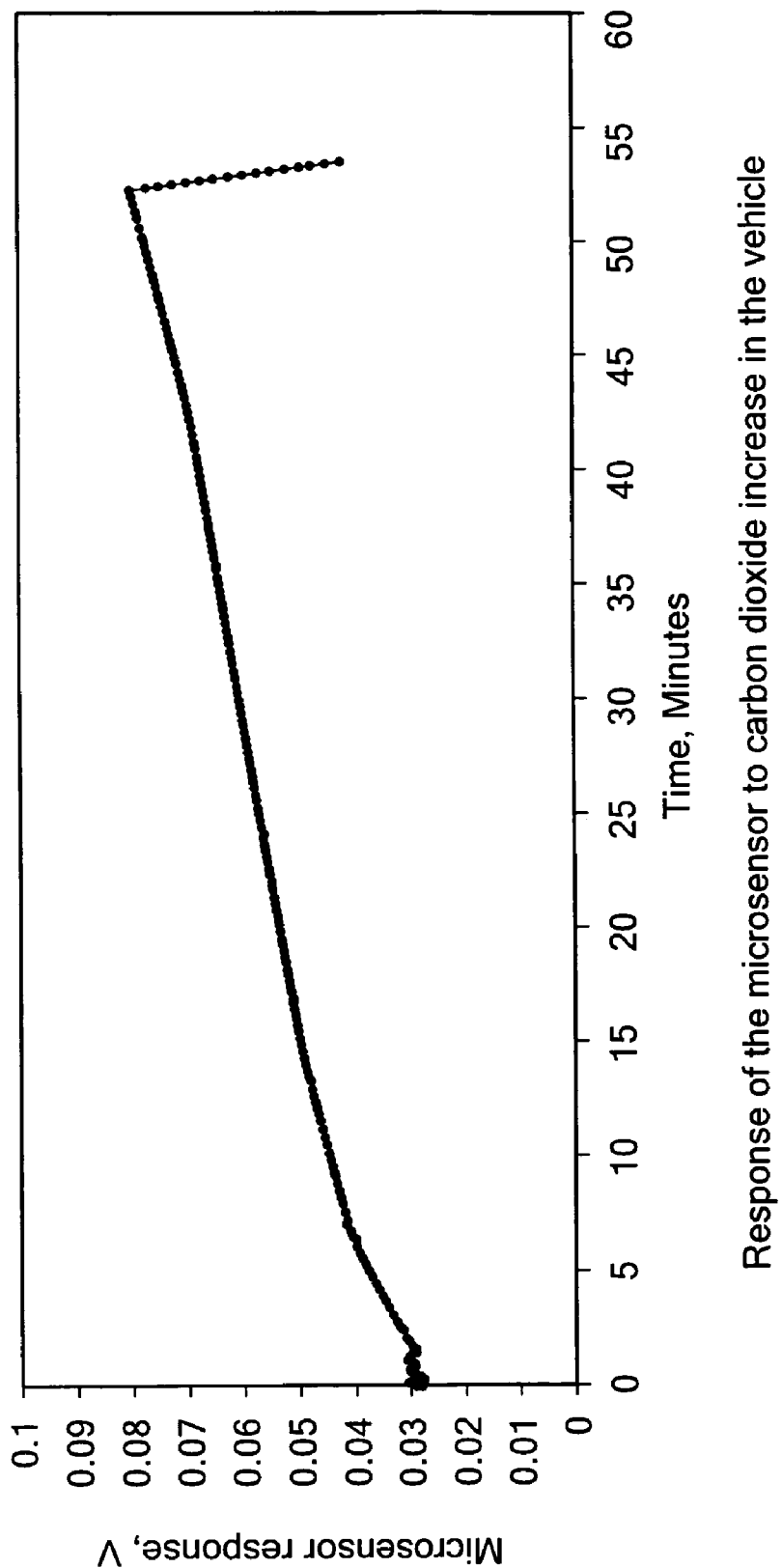

To simulate simultaneous detection of carbon dioxide increase and oxygen decrease due to presence of humans in a typical real-life situation, the microsensor assembly was placed in an automobile (Hyundai Elantra GLS) with an interior air volume of 2662.0 liters, and its performance for the detection of changes in carbon dioxide and oxygen caused by the presence of three (3) people (one in the driver's seat and two in the back seat) inside the vehicle was recorded wirelessly via a laptop computer. The microsensor assembly was placed on the armrest between the driver and passenger seats, and a laptop computer was placed on the passenger seat. FIGS. 11(a) and 11(b) show the results obtained for oxygen and carbon dioxide, respectively. The dotted lines in the figures illustrate the results when the vehicle doors were opened at the 52-minute mark.

Example 3

Simultaneous Detection of Carbon Dioxide and Oxygen in Cargo Shipping Container

Figure 12:
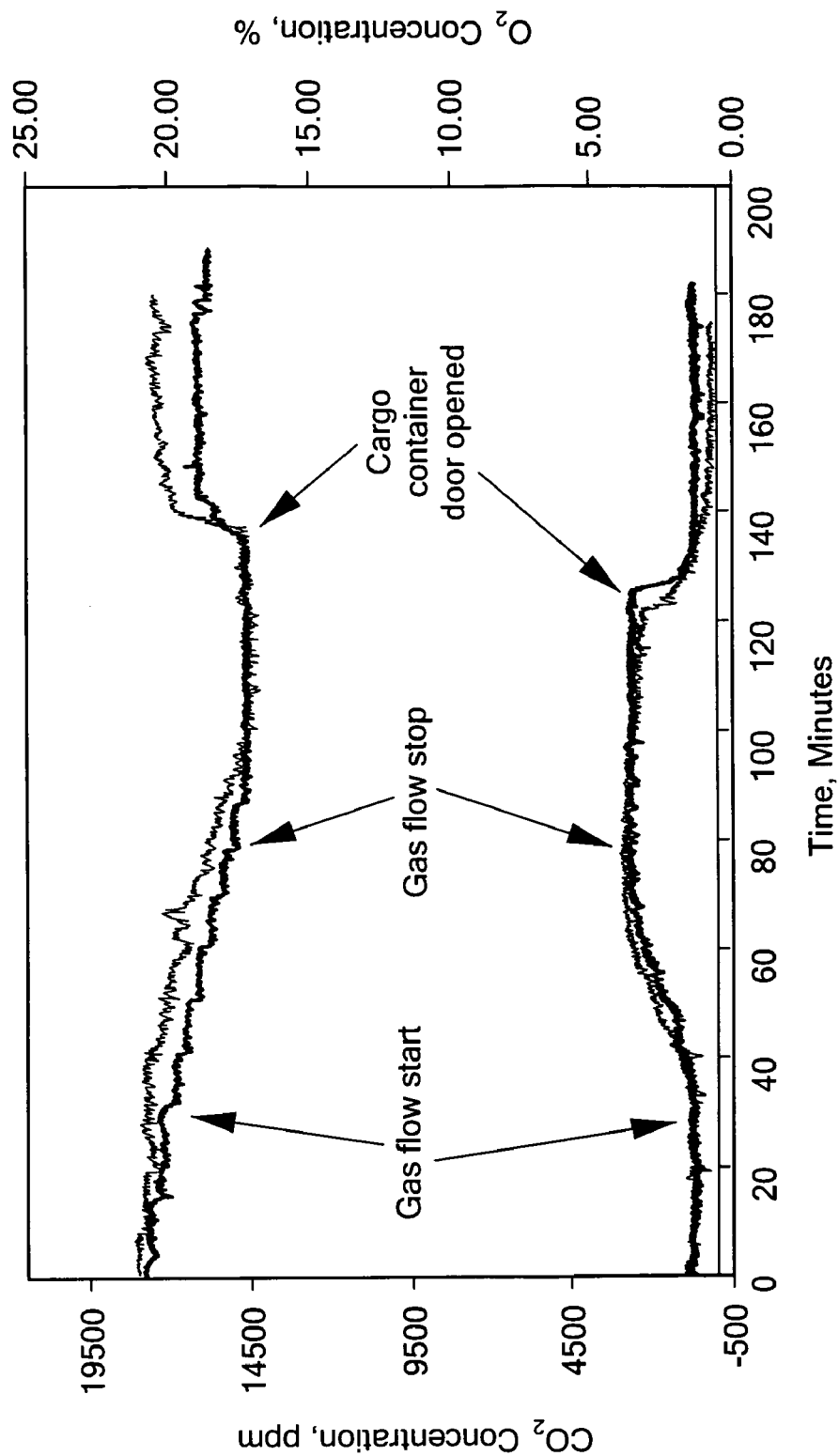
FIG. 12 shows the response curves obtained in Example 3 for the simultaneous detection of carbon dioxide and oxygen concentrations using the subject microsensor assembly and using commercial infra-red (IR)$CO_2$ and catalytic $O_2$ sensors.

To simulate the detection of stowaways in cargo shipping containers, the subject microsensor assembly was tested in a previously leased metal cargo shipping container (8'×8'×10'). The microsensor assembly was placed inside the container and exposed to outdoor air by keeping the container door open until a stable background was established, followed by exposure to a mixture of carbon dioxide/nitrogen to simulate an increase in nitrogen and concomitant decrease in the oxygen content in the container and increase of carbon dioxide concentration. Oxygen and carbon dioxide concentration change was achieved by flowing measured volumes of nitrogen and carbon dioxide from their respective cylinders placed inside the container. The container's door was closed and the microsensor's response wireless signals (carbon dioxide and oxygen) were recorded on a laptop computer. At the end of the experiment, the container's door was opened and the microsensor was exposed to outdoor air. FIG. 12 shows the response curves for simultaneous detection of carbon dioxide and oxygen concentrations and compares the results obtained using the subject microsensor assembly with commercial infra-red (IR)$CO_2$ and catalytic $O_2$ sensors.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:
1. A multi-gas microsensor assembly comprising:
 (a) a sensor module, said sensor module comprising
  (i) a sensor, said sensor comprising
   (A) a non-conductive solid substrate,
   (B) a plurality of sensing electrodes positioned on said non-conductive solid substrate,
   (C) a reference electrode positioned on said non-conductive solid substrate,
   (D) a counter electrode positioned on said non-conductive solid substrate,
   (E) wherein at least two of said sensing electrodes share said reference electrode and said counter electrode,
   (F) a solid polymer electrolyte ion-exchange membrane having a first side in intimate contact with each of said sensing electrodes, said reference electrode, and said counter electrode, said solid polymer electrolyte ion-exchange membrane having at least one gas diffusion opening aligned with each of said sensing electrodes,
   (G) wherein at least a portion of said reference electrode is positioned between the at least two sensing electrodes sharing said reference electrode and wherein at least a portion of said counter electrode is positioned between the at least two sensing electrodes sharing said counter electrode, and
  (ii) a sensor housing, the sensor housing having a cavity, the sensor being disposed within the cavity of the sensor housing; and
 (b) an electronics module, said electronics module comprising
  (i) an electronics housing, the electronics housing having a cavity,
  (ii) electronics disposed within the cavity of the electronics housing, said electronics including a multi-potentiostat, the multi-potentiostat being coupled to the sensor so as to simultaneously and independently control at least two of the sensing electrodes;
 (c) wherein one of the electronics module and the sensor module is positioned over the other.

2. The multi-gas microsensor assembly as claimed in claim 1 wherein said electronics further includes an electrical pulse generator electrically coupled to each of said metal oxide sensing electrode, said reference electrode, and said counter electrode, wherein the electrical pulse generator generates periodically at least one electrical pulse that simultaneously regenerates the metal oxide sensing electrode, the solid polymer electrolyte ion-exchange membrane, and the counter electrode.

3. The multi-gas sensor as claimed in claim 1, wherein said plurality of sensing electrodes includes a metal oxide sensing electrode and a gold sensing electrode.

4. The multi-gas microsensor assembly as claimed in claim 1 wherein the multi-potentiostat is coupled to the sensor using spring-loaded, electrically-conductive pins.

5. The multi-gas microsensor assembly as claimed in claim 4 further comprising a gasket, said electronics module being positioned over and in intimate contact with said gasket, said gasket being positioned over and in intimate contact with said sensor module.

6. The multi-gas microsensor assembly as claimed in claim 1 wherein said sensor housing comprises a base and a cover, said base having a recess, said sensor being disposed within said recess.

7. The multi-gas microsensor assembly as claimed in claim 6 wherein said recess comprises a lower portion and an upper portion, said sensor being disposed within said lower portion, and wherein said sensor module further comprises a tray, said tray being removably mounted within said upper portion of said recess.

8. The multi-gas microsensor assembly as claimed in claim 7 wherein said base further includes a water input, wherein said cover includes at least one gas input and, in fluid communication therewith, a first gas output and a second gas output, and wherein said tray includes a first gas channel in fluid communication with said first gas output of said cover and with said first sensing electrode, a second gas channel in fluid communication with said second gas output of said cover and with said second sensing electrode, a water reservoir, a water input in fluid communication both with said water reservoir and with said water input of said base, and a water output in fluid communication both with said water reservoir and with said lower portion of said recess.

9. A multi-gas microsensor assembly comprising:
 (a) a multi-gas sensor, said multi-gas sensor comprising
  (i) a non-conductive solid substrate, said non-conductive solid substrate having a first side,
  (ii) a plurality of sensing electrodes, each of said sensing electrodes being positioned on said first side of said non-conductive solid substrate,
  (iii) a reference electrode, said reference electrode being positioned on said first side of said non-conductive solid substrate,
  (iv) a counter electrode, said counter electrode being positioned on said first side of said non-conductive solid substrate,
  (v) wherein at least two of said sensing electrodes share said reference electrode and said counter electrode, and
  (vi) a solid polymer electrolyte ion-exchange membrane, said solid polymer electrolyte ion-exchange membrane having a first side in intimate contact with each of said sensing electrodes, said reference electrode, and said counter electrode, said solid polymer electrolyte ion-exchange membrane having at least one gas diffusion opening aligned with each of said sensing electrodes;

(vii) wherein at least a portion of said reference electrode is positioned between the at least two sensing electrodes sharing said reference electrode and wherein at least a portion of said counter electrode is positioned between the at least two sensing electrodes sharing said counter electrode; and (b) a multi-potentiostat, the multi-potentiostat simultaneously and independently controlling at least two of the sensing electrodes of the multi-gas sensor.

10. The multi-gas microsensor assembly as claimed in claim 9, wherein said solid polymer electrolyte ion-exchange membrane is a solid polymer electrolyte cation exchange membrane.

11. The multi-gas microsensor assembly as claimed in claim 9, wherein said multi-gas sensor is operated by said multi-potentiostat to detect at least two different gases simultaneously and in real time.

12. The multi-gas microsensor assembly as claimed in claim 11, wherein said plurality of sensing electrodes includes a metal oxide sensing electrode and a gold sensing electrode.

13. The multi-gas microsensor assembly as claimed in claim 12, wherein said plurality of sensing electrodes, said counter electrode and said reference electrode are made by screen-printing onto said non-conductive solid substrate.

14. The multi-gas microsensor assembly as claimed in claim 13, wherein the counter electrode comprises a material selected from the group consisting of silver and platinum, and wherein the reference electrode comprises a material selected from the group consisting of silver/silver chloride and Pt/air.

15. The multi-gas microsensor assembly as claimed in claim 14, wherein said solid polymer electrolyte ion-exchange membrane is a solid polymer electrolyte anion exchange membrane.

16. The multi-gas microsensor assembly as claimed in claim 15, wherein said solid polymer electrolyte anion exchange membrane is selected from the group consisting of a solid polymer electrolyte anion exchange membrane of a chloride ion form, a solid polymer electrolyte anion exchange membrane of a carbonate ion form, a solid polymer electrolyte anion exchange membrane of a bicarbonate ion form, a solid polymer electrolyte anion exchange membrane of a sulfate ion form, wherein the solid polymer electrolyte anion exchange membrane comprises a quaternary ammonium ion polymer or ionomer.

17. A multi-gas sensor, the multi-gas sensor comprising:
(a) a non-conductive solid substrate, said non-conductive solid substrate having a first side;
(b) a plurality of sensing electrodes, each of said sensing electrodes being positioned on said first side of said non-conductive solid substrate;
(c) a reference electrode, said reference electrode being positioned on said first side of said non-conductive solid substrate;
(d) a counter electrode, said counter electrode being positioned on said first side of said non-conductive solid substrate;
(e) wherein at least two of said sensing electrodes share said reference electrode and said counter electrode; and
(f) a solid polymer electrolyte ion-exchange membrane, said solid polymer electrolyte ion-exchange membrane having a first side in intimate contact with each of said sensing electrodes, said reference electrode, and said counter electrode, said solid polymer electrolyte ion-exchange membrane having at least one gas diffusion opening aligned with each of said sensing electrodes;
(g) wherein at least a portion of said reference electrode is positioned between the at least two sensing electrodes sharing said reference electrode and wherein at least a portion of said counter electrode is positioned between the at least two sensing electrodes sharing said counter electrode.

18. The multi-gas sensor as claimed in claim 17, wherein the plurality of sensing electrodes, the counter electrode, and the reference electrode are formed by screen printing.

19. The multi-gas sensor as claimed in claim 17, wherein the plurality of sensing electrodes, the counter electrode, and the reference electrode are arranged in a generally circular pattern, with a lead extending generally radially outwardly from each electrode.

20. The multi-gas sensor as claimed in claim 17, wherein said solid polymer electrolyte ion-exchange membrane is a solid polymer electrolyte cation exchange membrane.

21. The multi-gas sensor as claimed in claim 17, wherein said plurality of sensing electrodes consists of exactly two sensing electrodes.

22. The multi-gas sensor as claimed in claim 17, wherein the counter electrode has a surface area that exceeds the combined surface areas of the plurality of sensing electrodes.

23. The multi-gas sensor as claimed in claim 17, wherein the plurality of sensing electrodes consist of exactly two sensing electrodes and wherein the plurality of sensing electrodes, the counter electrode, and the reference electrode are arranged in a generally circular pattern, with each of the counter electrode and the reference electrode positioned alternately to the plurality of sensing electrodes.

24. The multi-gas sensor as claimed in claim 17, wherein the plurality of sensing electrodes consist of exactly two sensing electrodes, wherein the plurality of sensing electrodes, the counter electrode, and the reference electrode are arranged in a generally circular pattern, with each of the counter electrode and the reference electrode positioned alternately to the plurality of sensing electrodes, with a first lead extending generally radially outwardly from one of the sensing electrodes to a first contact pad on a first corner of the solid non-conductive substrate, a second lead extending generally radially outwardly from the counter electrode to a second contact pad on a second corner of the solid non-conductive substrate, a third lead extending generally radially outwardly from the other of the sensing electrodes to a third contact pad on a third corner of the solid non-conductive substrate, and a fourth lead extending generally radially outwardly from the reference electrode to a fourth contact pad at a fourth corner of the non-conductive solid substrate.

25. The multi-gas sensor as claimed in claim 24 further comprising an insulator, the insulator having a generally annular shape and covering the second and fourth leads but not covering the first and third leads, the first, second, third and fourth contact pads, and the plurality of sensing electrodes, the reference electrode and the counter electrode.

26. The multi-gas sensor as claimed in claim 17, wherein said plurality of sensing electrodes includes a metal oxide sensing electrode and a gold sensing electrode.

27. The multi-gas sensor as claimed in claim 26, wherein said metal oxide is selected from the group consisting of at least one of ruthenium oxide and iridium oxide.

28. The multi-gas sensor as claimed in claim 26, wherein said solid substrate comprises at least one of an inorganic material and an organic polymer, the inorganic material being selected from the group consisting of alumina, silica and titania, the organic polymer being selected from the group consisting of polyesters, polyimides, polysulfones, polyethers, polystyrenes, polyethylenes, polypropylenes, polycarbonates, and liquid crystal polymers.

29. The multi-gas sensor as claimed in claim 26, wherein the counter electrode comprises a material selected from the group consisting of silver and platinum and wherein the reference electrode comprises a material selected from the group consisting of silver/silver chloride and Pt/air.

30. The multi-gas sensor as claimed in claim 26, wherein said solid polymer electrolyte ion-exchange membrane is a solid polymer electrolyte anion exchange membrane.

31. The multi-gas sensor as claimed in claim 30, wherein said solid polymer electrolyte anion exchange membrane is selected from the group consisting of a solid polymer electrolyte anion exchange membrane of a chloride ion form, a solid polymer electrolyte anion exchange membrane of a carbonate ion form, a solid polymer electrolyte anion exchange membrane of a bicarbonate ion form, a solid polymer electrolyte anion exchange membrane of a sulfate ion form, wherein the solid polymer electrolyte anion exchange membrane comprises a quaternary ammonium ion polymer or ionomer.

* * * * *